United States Patent
Schraga

(10) Patent No.: US 8,066,728 B2
(45) Date of Patent: Nov. 29, 2011

(54) DISPOSABLE OR SINGLE-USE LANCET DEVICE AND METHOD

(75) Inventor: Steven Schraga, Surfside, FL (US)

(73) Assignee: Stat Medical Devices, Inc., Miami, FL (US)

( * ) Notice: Subject to any disclaimer, the term of this patent is extended or adjusted under 35 U.S.C. 154(b) by 1304 days.

(21) Appl. No.: 10/998,636

(22) Filed: Nov. 30, 2004

(65) Prior Publication Data

US 2006/0116705 A1   Jun. 1, 2006

(51) Int. Cl.
*A61B 17/32* (2006.01)
(52) U.S. Cl. .................................. 606/182; 606/181
(58) Field of Classification Search ............. 606/182, 606/181; 600/583, 584
See application file for complete search history.

(56) References Cited

U.S. PATENT DOCUMENTS

| | | | |
|---|---|---|---|
| 676,678 A | 6/1901 | Ellifrits | |
| 1,135,465 A | 4/1915 | Pollock | |
| 2,848,809 A | 2/1956 | Crowder | |
| 2,823,677 A | 2/1958 | Hein, Jr. | |
| 3,589,213 A | 6/1971 | Gourley | |
| 3,760,809 A | 9/1973 | Campbell, Jr. | |
| 4,064,871 A | 12/1977 | Reno | |
| 4,139,011 A | 2/1979 | Benoit et al. | |
| 4,157,086 A | 6/1979 | Maiorano et al. | |
| 4,203,446 A | 5/1980 | Hofert et al. | |
| 4,257,561 A | 3/1981 | McKinney | |
| 4,388,925 A | 6/1983 | Burns | |
| 4,426,105 A | 1/1984 | Plaquin et al. | |
| 4,438,770 A | 3/1984 | Unger et al. | |
| 4,449,529 A | 5/1984 | Burns et al. | |
| 4,469,110 A | 9/1984 | Slama | |
| 4,517,978 A | 5/1985 | Levin et al. | |
| 4,527,561 A | 7/1985 | Burns | |
| 4,539,988 A | 9/1985 | Shirley et al. | |
| 4,553,541 A | 11/1985 | Burns | |
| 4,628,929 A | 12/1986 | Intengan et al. | |
| 4,643,189 A | 2/1987 | Mintz | |
| 4,653,513 A * | 3/1987 | Dombrowski | 600/578 |
| 4,785,858 A | 11/1988 | Valentini et al. | |
| 4,817,603 A * | 4/1989 | Turner et al. | 606/182 |
| RE32,922 E | 5/1989 | Levin et al. | |
| 4,834,667 A | 5/1989 | Fowler et al. | |

(Continued)

FOREIGN PATENT DOCUMENTS

CA      523078      3/1956

(Continued)

OTHER PUBLICATIONS

Sutor et al., ABleeding from Standardized Skin Punctures: Automated Technic for Recording Time, Intensity, and Pattern of Bleeding@, *A.J.C.P.*, vol. 55, pp. 541-549 (May 1971).

(Continued)

*Primary Examiner* — Tuan Nguyen
(74) *Attorney, Agent, or Firm* — Greenblum & Bernstein, P.L.C.

(57) ABSTRACT

Single-use lancet device includes a body. A movable skin engaging member is at least partially disposed inside the body and includes a lancet opening through which a lancet needle extends. A holding member can move at least between a retracted position and an extended position. The skin engaging member is structured and arranged to retract into the body. This Abstract is not intended to define the invention disclosed in the specification, nor intended to limit the scope of the invention in any way.

65 Claims, 28 Drawing Sheets

U.S. PATENT DOCUMENTS

| | | |
|---|---|---|
| 4,858,607 A | 8/1989 | Jordan et al. |
| 4,869,249 A | 9/1989 | Crossman et al. |
| 4,895,147 A | 1/1990 | Bodicky et al. |
| 4,924,879 A | 5/1990 | O'Brien |
| 4,976,724 A | 12/1990 | Nieto et al. |
| 4,990,154 A | 2/1991 | Brown et al. |
| 5,074,872 A | 12/1991 | Brown et al. |
| 5,133,730 A | 7/1992 | Biro et al. |
| 5,147,375 A | 9/1992 | Sullivan et al. |
| 5,212,879 A | 5/1993 | Biro et al. |
| 5,269,799 A | 12/1993 | Daniel |
| 5,282,822 A | 2/1994 | Macors et al. |
| 5,304,193 A | 4/1994 | Zhadanov |
| 5,314,441 A | 5/1994 | Cusack et al. |
| 5,318,584 A | 6/1994 | Lange et al. |
| 5,324,303 A | 6/1994 | Strong et al. |
| 5,350,392 A | 9/1994 | Purcell et al. |
| 5,356,420 A | 10/1994 | Czernecki et al. |
| 5,366,470 A | 11/1994 | Ramel |
| 5,395,388 A | 3/1995 | Schraga |
| 5,423,847 A | 6/1995 | Strong et al. |
| 5,439,473 A * | 8/1995 | Jorgensen ............... 606/182 |
| 5,454,828 A | 10/1995 | Schraga |
| 5,464,418 A | 11/1995 | Schraga |
| 5,476,101 A | 12/1995 | Schramm et al. |
| 5,509,345 A | 4/1996 | Cyktich |
| 5,518,004 A | 5/1996 | Schraga |
| 5,527,333 A | 6/1996 | Nikkels et al. |
| 5,527,334 A | 6/1996 | Kanner et al. |
| 5,529,581 A | 6/1996 | Cusack |
| 5,540,709 A * | 7/1996 | Ramel ............... 606/183 |
| 5,545,174 A | 8/1996 | Schenk et al. |
| 5,554,166 A | 9/1996 | Lange et al. |
| 5,569,286 A | 10/1996 | Peckham et al. |
| 5,569,287 A | 10/1996 | Tezuka et al. |
| 5,571,132 A | 11/1996 | Mawhirt et al. |
| D376,203 S | 12/1996 | Schraga |
| 5,613,978 A | 3/1997 | Harding |
| 5,628,764 A | 5/1997 | Schraga |
| 5,628,765 A | 5/1997 | Morita |
| 5,643,306 A | 7/1997 | Schraga |
| 5,662,672 A | 9/1997 | Pambianchi et al. |
| 5,707,384 A * | 1/1998 | Kim ............... 606/181 |
| 5,730,753 A | 3/1998 | Morita |
| 5,733,300 A | 3/1998 | Pambianchi et al. |
| 5,741,288 A | 4/1998 | Rife |
| RE35,803 E | 5/1998 | Lange et al. |
| 5,772,677 A | 6/1998 | Mawhirt et al. |
| 5,797,940 A | 8/1998 | Mawhirt et al. |
| 5,797,942 A | 8/1998 | Schraga |
| 5,873,887 A | 2/1999 | King et al. |
| 5,879,367 A | 3/1999 | Latterell et al. |
| 5,908,434 A | 6/1999 | Schraga |
| 5,916,230 A | 6/1999 | Brenneman et al. |
| 5,984,940 A | 11/1999 | Davis et al. |
| 6,010,519 A | 1/2000 | Mawhirt et al. |
| 6,022,366 A | 2/2000 | Schraga |
| 6,042,595 A | 3/2000 | Morita |
| 6,045,567 A | 4/2000 | Taylor et al. |
| 6,056,765 A | 5/2000 | Bajaj et al. |
| 6,071,294 A | 6/2000 | Simons et al. |
| D428,150 S | 7/2000 | Ruf et al. |
| 6,136,013 A | 10/2000 | Marshall et al. |
| 6,152,942 A | 11/2000 | Brenneman et al. |
| 6,156,050 A | 12/2000 | Davis et al. |
| 6,156,051 A | 12/2000 | Schraga |
| 6,168,606 B1 * | 1/2001 | Levin et al. ............... 606/181 |
| 6,183,489 B1 | 2/2001 | Douglas et al. |
| 6,190,398 B1 | 2/2001 | Schraga |
| 6,192,891 B1 | 2/2001 | Gravel et al. |
| 6,197,040 B1 | 3/2001 | LeVaughn et al. |
| 6,210,420 B1 | 4/2001 | Mauze et al. |
| 6,221,089 B1 | 4/2001 | Mawhirt |
| 6,228,100 B1 | 5/2001 | Schraga |
| 6,258,112 B1 * | 7/2001 | Schraga ............... 606/181 |
| 6,283,982 B1 | 9/2001 | Le Vaughn et al. |
| 6,306,152 B1 | 10/2001 | Verdonk et al. |
| 6,319,210 B1 * | 11/2001 | Douglas et al. ............... 600/583 |
| 6,322,574 B1 | 11/2001 | Lloyd et al. |
| 6,322,575 B1 | 11/2001 | Schraga |
| 6,332,871 B1 | 12/2001 | Douglas et al. |
| 6,346,114 B1 | 2/2002 | Schraga |
| 6,358,265 B1 | 3/2002 | Thorne, Jr. et al. |
| 6,364,889 B1 | 4/2002 | Kheiri et al. |
| 6,379,317 B1 | 4/2002 | Kintzig et al. |
| 6,395,495 B1 | 5/2002 | Montagnier et al. |
| 6,409,740 B1 | 6/2002 | Kuhr et al. |
| 6,419,661 B1 * | 7/2002 | Kuhr et al. ............... 604/207 |
| 6,451,040 B1 | 9/2002 | Purcell |
| 6,464,649 B1 | 10/2002 | Duchon et al. |
| 6,506,168 B1 | 1/2003 | Fathallah et al. |
| 6,514,270 B1 | 2/2003 | Schraga |
| 6,540,762 B1 | 4/2003 | Bertling |
| 6,558,402 B1 | 5/2003 | Chelak et al. |
| 6,997,936 B2 * | 2/2006 | Marshall ............... 606/181 |
| 2002/0087180 A1 * | 7/2002 | Searle et al. ............... 606/181 |

FOREIGN PATENT DOCUMENTS

| | | |
|---|---|---|
| EP | 0061102 | 9/1982 |
| EP | 0137975 | 4/1985 |
| EP | 0189117 | 7/1986 |
| EP | 0885590 | 12/1998 |
| EP | 0904731 | 3/1999 |
| EP | 1074219 | 2/2001 |

OTHER PUBLICATIONS

U.S. Appl. No. 11/052,738 in the name of Schraga entitled "A Single Use Lancet Device", filed Feb. 7, 2005.

U.S. Appl. No. 10/988,636 in the name of Schraga entitled "Single-Use Blade Lancet Device", filed Nov. 16, 2004.

* cited by examiner

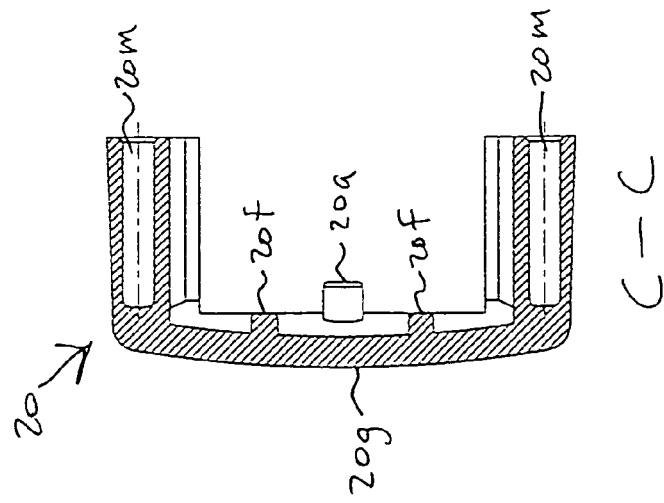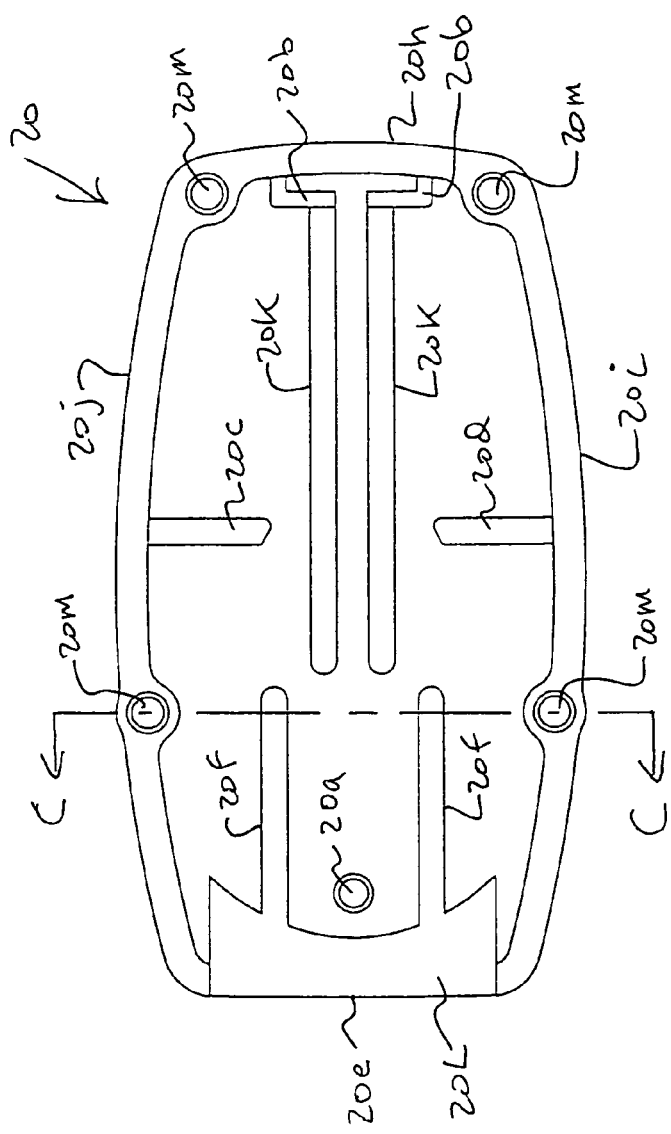

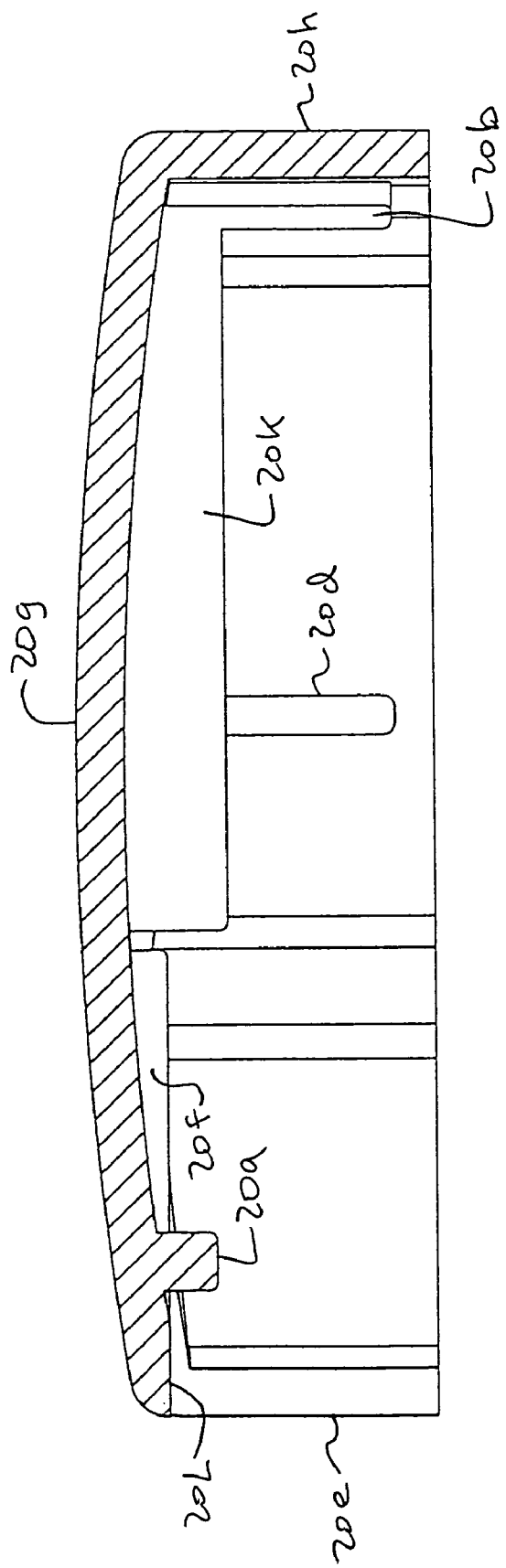

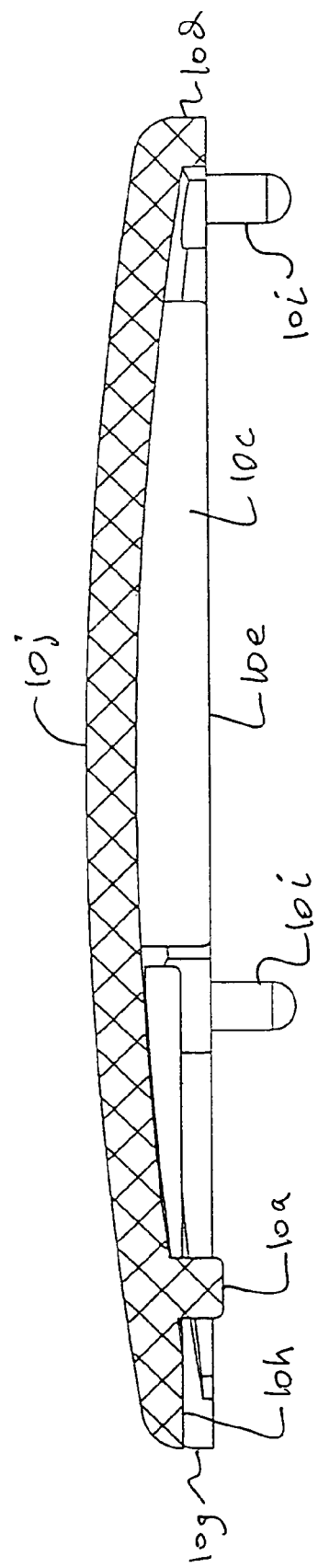

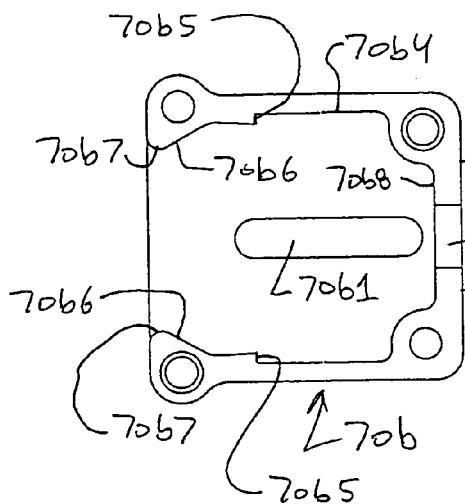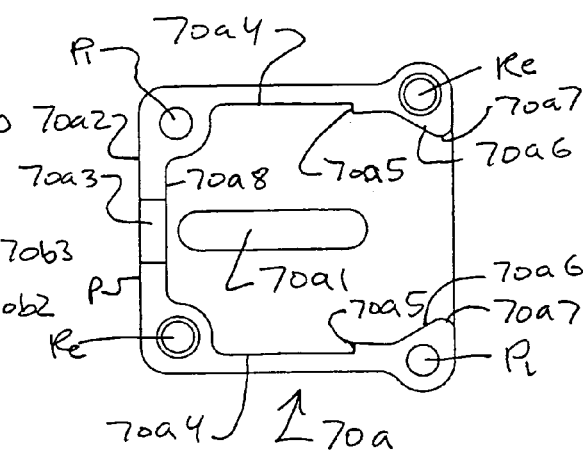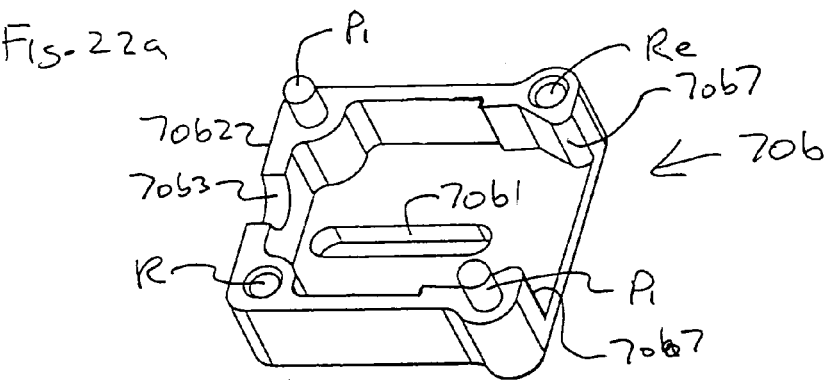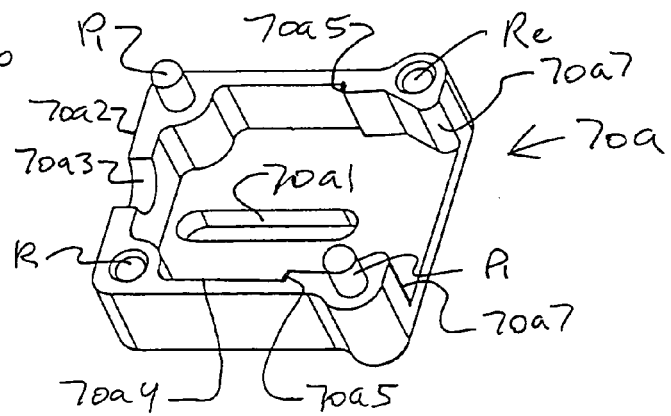

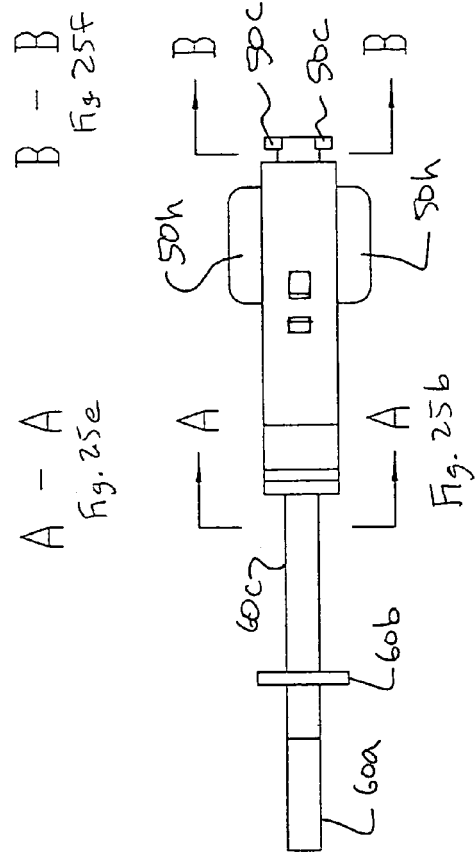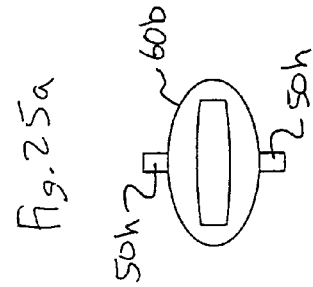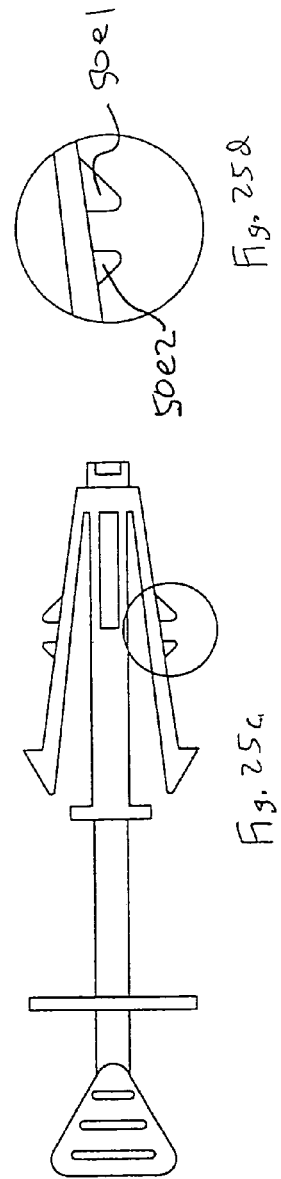

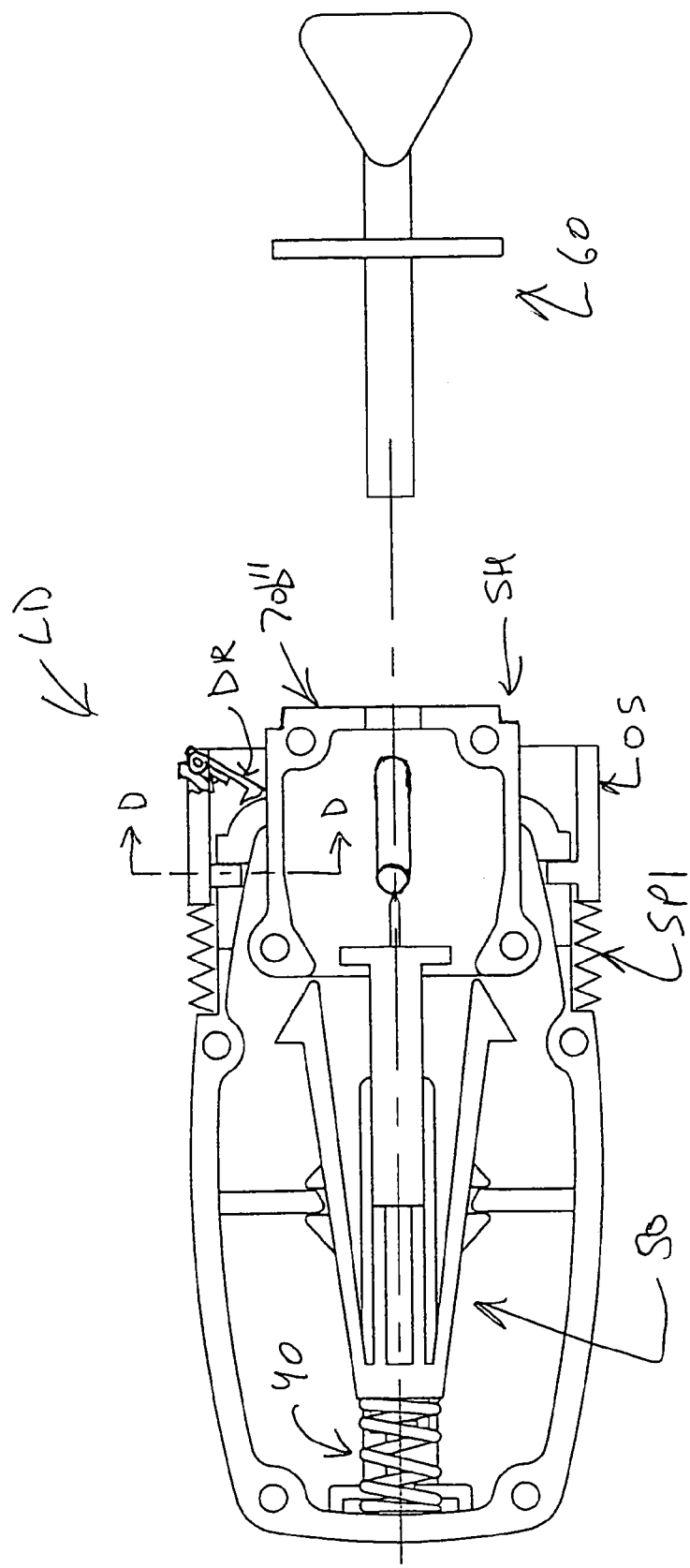

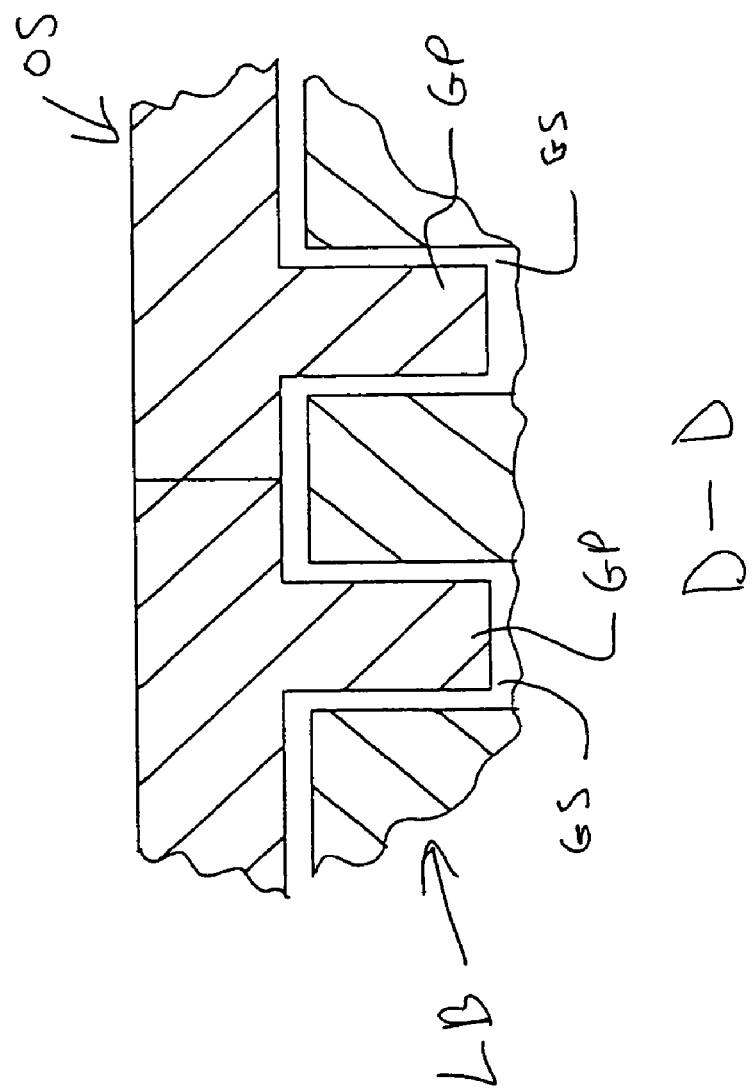

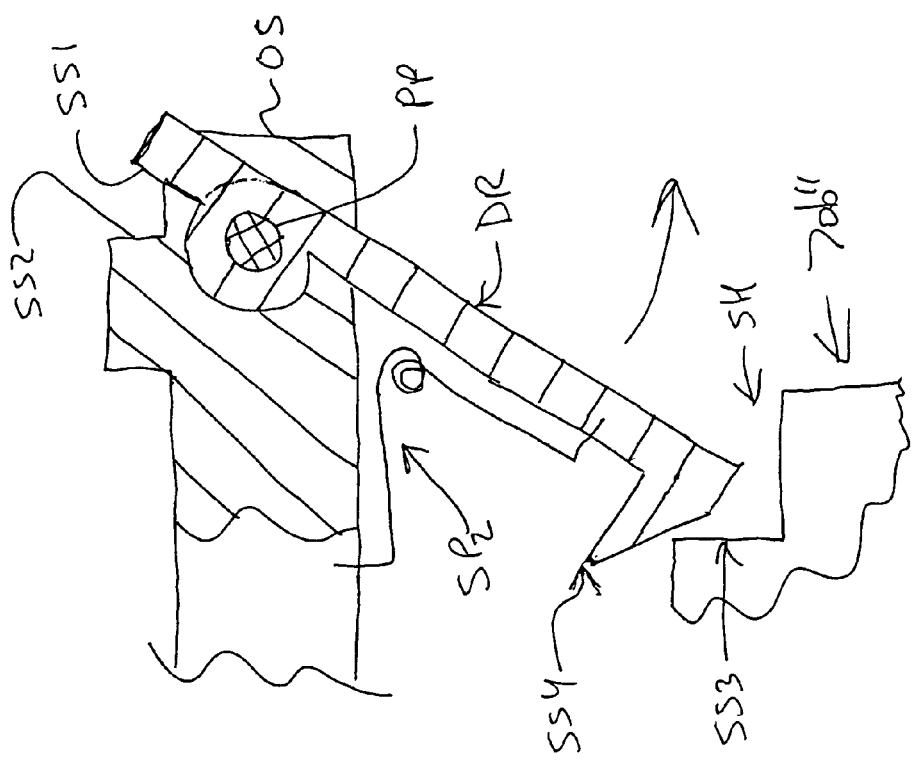

DISPOSABLE OR SINGLE-USE LANCET DEVICE AND METHOD

BACKGROUND OF THE INVENTION

1. Field of the Invention

The invention relates to a lancet device having a skin engaging surface which can be covered and/or protected after use of the lancet device. The invention also relates to a disposable and/or single-use lancet device having a retractable skin engaging portion, and to a method of using a disposable and/or single-use lancet device. In particular, the invention relates to a lancet device which may be disposable, i.e., which can be used once and discarded, and/or which utilizes an arrangement which protects a user from contacting his or her skin with the same surface of the skin engaging portion after the device has been triggered and/or fired.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Additionally, many users simply cannot perform the procedure owing to either a fear of needles or because they lack a steady hand. As a result, lancet devices have been developed which allow the user to more easily and reliably perform this procedure.

Known single-use/disposable lancet devices are not sufficiently and/or properly design to ensure that they cannot be reused. Moreover, such devices generally do not protect a user from coming into contact with body fluids such as blood which may be on the device after the device has been used.

An improved device would allow the user to use the device only a single time and more reliably and safely prevent reuse of the device. The device should also ensure that a contaminated surface of the device cannot come into contact with a user after the device is used. Finally, an improved device should be safe to dispose of, should be simple in design, and should be inexpensive to produce.

SUMMARY OF THE INVENTION

According to one illustrative aspect of the invention there is provided a disposable and/or single-use lancet device that includes a body. A skin engaging member is movable with respect to the body and comprises a lancet opening through which a lancet needle extends. A holding member is movably mounted within the body and comprises a front end and a rear end. The holding member is movable at least between a retracted position and an extended position. A first stop surface moves with the skin engaging member. A second stop surface moves with the holding member. Movement of the skin engaging member from an initial position to a triggering position causes the holding member to move towards the extended position and once caused to move to the extended position, the holding member is prevented from moving back to the retracted position.

Once caused to move to the triggering position, the skin engaging member may also be prevented from moving back to the initial position.

The lancet device may further comprise a spring, wherein the spring causes the holding member to move to the extended position and prevents the holding member from moving back to the retracted position. The spring may cause the skin engaging member to move to a retracted position, whereby the skin engaging member is disposed within the body.

The lancet device may further comprise a spring which causes the skin engaging member and the holding member to move into the body after the lancet device is triggered.

The lancet device may further comprise a spring which causes movement of the holding member between the retracted position and the extended position and between the extended position and an intermediate position.

The lancet device may further comprise a spring which causes the holding member to move away from the lancet opening after the lancet device is triggered. The holding member may cause the skin engaging member to move into the body after the lancet device is triggered.

The holding member may cause the skin engaging member to move into the body after the lancet device is triggered.

The lancet device may further comprise a compression spring for biasing the holding member towards the extended position. The compression spring may comprise one end that is fixed to the rear end of the holding member and another end that is fixed to the body. The compression spring may comprise one end that is connected to the holding member and another end that is connected to the body.

The lancet device may be automatically triggered by movement of the skin engaging portion.

The body may comprise an upper housing part and a lower housing part. The upper housing part may comprise a cover and the lower housing part may comprise a main body portion.

The holding member may comprise the lancet needle and at least one deflectable arm. The holding member may comprise at least one integrally formed deflectable arm. The holding member may comprise two oppositely arranged integrally formed deflectable arms. The holding member may comprise a mechanism for releasably engaging with at least one flange fixed inside the body.

The holding member may comprise two mechanisms for releasably engaging with two flanges fixed inside the body. The holding member may comprise two oppositely arranged integrally formed deflectable arms. One of the two mechanisms may be arranged on one of the two integrally formed deflectable arms and another of the two mechanisms may be arranged on another of the two integrally formed deflectable arms.

The holding member may comprise two mechanisms for releasably engaging with two projections fixed inside the body. The holding member may comprise two oppositely arranged deflectable arms. One of the two mechanisms may be arranged on one of the two deflectable arms and another of the two mechanisms may be arranged on another of the two deflectable arms.

The holding member may comprise two oppositely arranged deflectable arms, each deflectable arm comprising two projections and a space disposed between the two projections, whereby each space receives therein a projecting portion fixed within the body when the holding member is in the retracted position.

The holding member may comprise a removable tab portion. The holding member may comprise a mechanism for preventing accidental triggering of the lancet device. The mechanism for preventing accidental triggering of the lancet device may comprise a removable tab portion coupled to the front end of the holding member.

The front end of the holding member may hold the lancet needle. The lancet needle may project from the front end of the holding member. The second stop surface may be arranged on the front end of the holding member and behind a tip of the lancet needle.

The lancet device may further comprise a removable trigger preventing device, whereby the lancet device cannot be triggered without removing the trigger preventing device.

The lancet device may further comprise a removable trigger preventing device, whereby the lancet device cannot be triggered or used without disconnecting the trigger preventing device from the front end of the holding member. The removable trigger preventing device may comprise a gripping portion, a flange which engages the skin engaging member, and an end adapted to cover the lancet needle. The removable trigger preventing device may comprise a gripping portion, a flange which engages the skin engaging member, and an end removably connected to the front of the holding member and adapted to cover the lancet needle.

The skin engaging member may be configured to slide into the body during triggering of the lancet device. The skin engaging member may comprise at least one straight and/or planar surface which slidably engages at least one straight and/or planar surface of the body during triggering of the lancet device.

The skin engaging member may comprise a generally rectangular cross-sectional shape. An inside surface of the skin engaging member may comprise the first stop surface.

The body may comprise a mechanism for guiding an axial movement of the holding member. The mechanism for guiding may comprise at least two projecting flanges arranged inside the body. The holding member may comprise at least one projecting portion which moves with a space disposed between the at least two projecting flanges. The mechanism for guiding may comprise oppositely arranged projecting flanges arranged inside the body. The holding member may comprise two oppositely arranged projecting portions which move with spaces disposed between the oppositely arranged projecting flanges. The holding member may comprise ends which engage internal shoulders of the skin engaging member when the holding member moves from the extended position to an intermediate position.

The body may comprise a two-piece body. The skin engaging member may comprise at least one recess which receives therein a projection extending into the body. The skin engaging member may comprise oppositely arranged recesses which each receive therein a projection fixed to the body.

The invention also provides for a method of puncturing a surface of skin using any of the lancet devices described above wherein the method comprises disposing the skin engaging member of the lancet device against a user's skin, moving the skin engaging portion relative to the body so as to cause automatic triggering of the lancet device, whereby the lancet needle is caused to penetrate the user's skin, and preventing the user from moving the holding member to the retracted position.

The invention also provides for a method of puncturing a surface of skin using any of the lancet devices described above wherein the method comprises disposing the skin engaging member of the lancet device against a user's skin, moving the skin engaging portion relative to the body so as to cause automatic triggering of the lancet device, whereby the lancet needle is caused to penetrate the user's skin, preventing the user from moving the holding member to the retracted position, and preventing the user from moving the skin engaging member to the initial position.

The invention also provides for a method of puncturing a surface of skin using any of the lancet devices described above wherein the method comprises disposing the skin engaging member of the lancet device against a user's skin, and moving the skin engaging portion relative to the body so as to cause automatic triggering of the lancet device, whereby the holding member is caused to move to the extended position and the lancet needle is caused to penetrate the user's skin, wherein, after triggering, the user is at least one of prevented from moving the holding member to the retracted position and prevented from moving the skin engaging member to the initial position.

The invention also provides for a method of using any of the lancet devices described above wherein the method comprises removing a triggering prevention device, disposing the skin engaging member of the lancet device against a user's skin, and moving the skin engaging member relative the body, wherein the moving automatically causes movement of the holding member towards the extended position.

The invention also provides for a method of using any of the lancet devices described above wherein the method comprises removing a triggering prevention device, disposing the skin engaging member of the lancet device against a user's skin, and non-rotatably moving the skin engaging member relative to the body, wherein the non-rotatably moving automatically causes movement of the holding member towards the extended position.

The invention also provides for a single-use lancet device which comprises a body. A skin engaging member is at least partially disposed inside the body and comprises a lancet opening through which a lancet needle extends. A holding member is movably mounted within the body and comprising a front end and a rear end. The holding member is movable at least between a retracted position and an extended position. A first stop surface moves with the skin engaging member. A second stop surface moves with the holding member. Movement of the skin engaging member from an initial position to a triggering position automatically causes the holding member to move towards the extended position.

Once caused to move to the extended position, the holding member may be prevented from moving back to the retracted position. Once caused to move to the triggering position, the skin engaging member may be prevented from moving back to the initial position.

The lancet device may further comprise a spring, wherein the spring causes the holding member to move to the extended position and prevents the holding member from moving back to the retracted position.

The lancet device may further comprise a spring which causes movement of the holding member between the retracted position and the extended position and between the extended position and an intermediate position.

The holding member may cause the skin engaging member to move further into the body after the lancet device is triggered. The holding member may cause the skin engaging member to move into the body after the lancet device is triggered.

The invention also provides for a single-use lancet device which comprises a body. A non-rotatably and slidable mounted skin engaging member is at least partially disposed inside the body. The skin engaging member comprises a lancet opening through which a lancet needle extends. A holding member is movably mounted within the body and comprises a front end and a rear end. The holding member is movable at least between a retracted position and an extended position. Movement of the skin engaging member further into the body may cause the holding member to automatically move towards the extended position.

The invention also provides for a single-use lancet device which comprises a body. A movable skin engaging member is at least partially disposed inside the body and comprises a lancet opening through which a lancet needle extends. A holding member can move at least between a retracted position and an extended position. The skin engaging member is structured and arranged to retract into the body.

The invention also provides for a lancet device which comprises a body, a skin engaging member, a lancet opening through which a lancet needle extends, a holding member which can move at least between a retracted position and an extended position, and at least one of: at least after the holding member moves to the extended position, the skin engaging member is covered by at least one of an outer sleeve and a portion of the body; at least after triggering of the lancet device, a front edge of at least one of an outer sleeve and a portion of the body extends forwardly of a skin contact surface of the skin engaging member; at least after the holding member moves to the extended position, the skin engaging member is covered by at least one of an outer sleeve and a portion of the body, and at least after triggering of the lancet device, a front edge of at least one of an outer sleeve and a portion of the body extends forwardly of a skin contact surface of the skin engaging member.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 13 shows a top view of the lancet body member used in the embodiment shown in FIGS. 1-12;

FIG. 14 shows a cross-section view through section C-C of FIG. 13;

FIG. 15 shows a center cross-section view of the lancet body member shown in FIG. 13. The section shown is perpendicular to section C-C;

FIG. 19 shows a center cross-section view of the lancet body cover shown in FIG. 17;

FIG. 21a shows an inside view of a lower part of the skin engaging member used in the embodiment shown in FIGS. 1-12;

FIG. 21b shows an inside view of an upper part of the skin engaging member used in the embodiment shown in FIGS. 1-12;

FIG. 22a shows a perspective inside view of the lower part shown in FIG. 21a;

FIG. 22b shows a perspective inside view of the upper part shown in FIG. 21b;

FIG. 23a shows another inside perspective view of the lower part shown in FIGS. 21a and 22a;

FIG. 25a shows an end view of the tab portion of the lancet mechanism shown in FIG. 24;

FIG. 25b shows a side view the lancet mechanism of FIG. 24 in an assembled state with the tab portion being connected to the lancet holding member portion;

FIG. 25c shows a top view of the lancet mechanism of FIG. 25b;

FIG. 25d shows a partial enlarged view of the circled portion shown in FIG. 25c;

FIG. 25e shows a cross-section view through section A-A of FIG. 25b. The two arms of the lancet holder portion are not shown;

FIG. 25f shows a cross-section view through section B-B of FIG. 25b;

FIGS. 26a-26e show another embodiment of a lancet device in various positions wherein:

FIG. 26a shows the tab portion being removed;

FIG. 26b shows the skin engaging head being moved back manually via a button until the two arms of the lancet holder portion disengage from the retaining flanges;

FIG. 26c shows the lancet holder portion after it has moved forward under the action of the spring and the lancet needle has passed through the lancet opening so as to pierce the skin of a user;

FIG. 26d shows the two arms of the lancet holder portion having been deflected outwards until they engage inside surfaces of the skin engaging head;

FIG. 26e shows the lancet holder portion having moved back under the action of the spring. The lancet needle has also retracted back behind the shin engaging surface of the skin engaging head. The button has also become locked to the lancet body so that the skin engaging head cannot be moved forward again;

FIG. 27b shows a partial end view of FIG. 27a;

FIG. 28 shows another embodiment of a lancet device. This device is similar to the one shown in FIGS. 1-11 and additionally utilizes an outer sleeve member to ensure that the device cannot be used again and/or to inform the user that the device has been used and/or to provide an additional mechanism that prevents contact between the potentially contaminated skin engaging surface and the device after use;

FIG. 29 shows a partial cross-section of section D-D of FIG. 28;

FIG. 30 shows an enlarged view of a portion of FIG. 28;

FIGS. 31-34 show another embodiment of a lancet device in various positions wherein:

FIG. 31 shows a front portion of the lancet device with the tab portion installed therein;

FIG. 32 shows the lancet device with the tab portion removed and the skin engaging head being moved back in a manner similar to that described with regard to FIG. 6;

FIG. 33 shows the lancet device after the inner sleeve has been moved forward manually; and FIG. 34 shows one non-limiting way in which the inner sleeve can be locked in the fully extended forward position.

DETAILED DESCRIPTION OF THE PRESENT INVENTION

Figure 1:
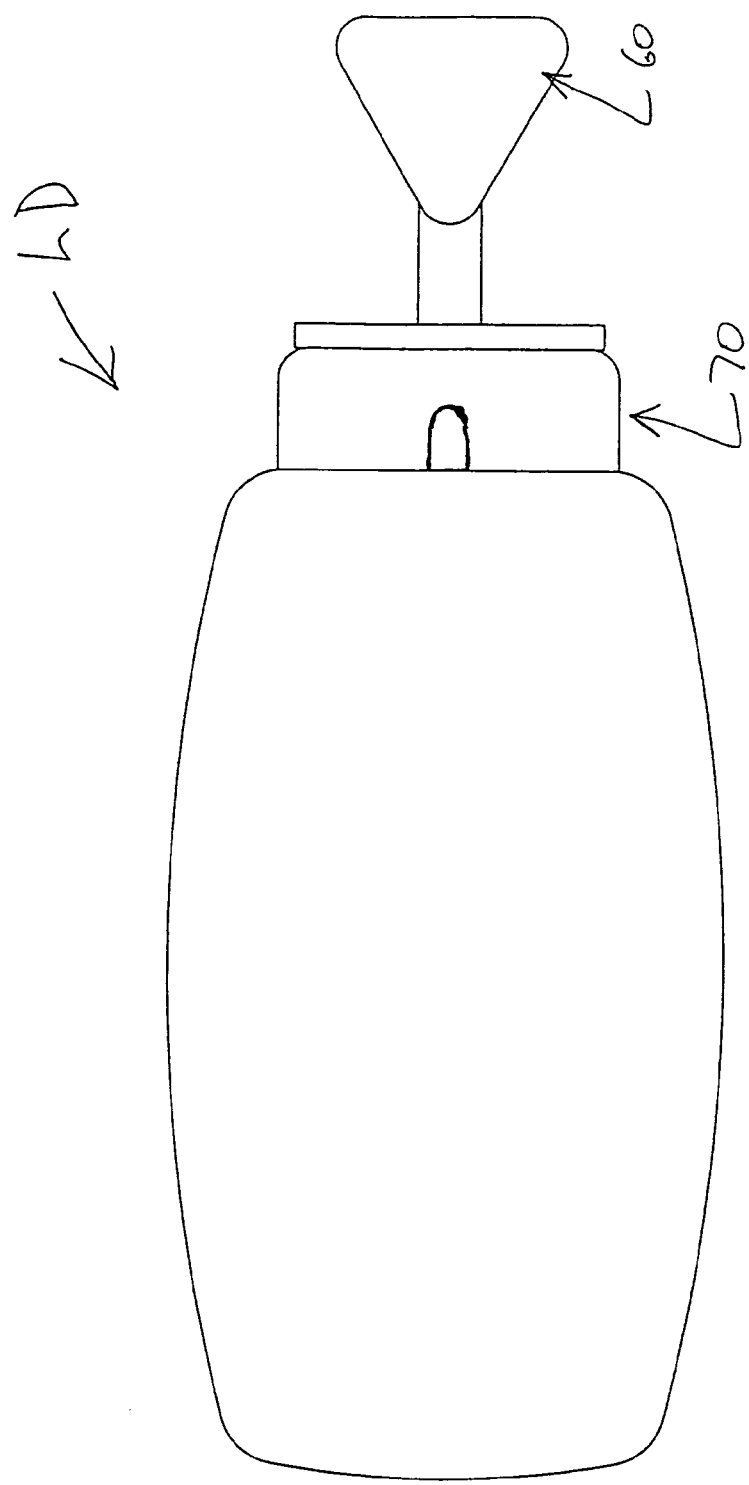
FIG. 1 shows a top view of one embodiment of the single-use lancet device. The device is shown in the loaded (trigger set) position and the trigger prevention device is shown installed on the lancet device.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-25 show a first non-limiting embodiment of a single-use and/or disposable lancet device LD. Lancet device LD has a lancet body made up of an upper or front cover portion 10 and a lower or rear body portion 20. These parts 10 and 20 are connected to each other, e.g., using adhesives and/or fasteners and/or welding and/or preferably snap-together holding mechanisms (such as pins and receiving openings), when the lancet device is initially assembled. A lancet mechanism 30 is arranged within the lancet body and includes a holding member portion 50 which is movably disposed within the body parts 10, 20 (see FIGS. 5-11) and a tab member portion 60. As will be described in detail later on, the tab member portion 60 functions as triggering prevention device.

As with many lancet devices, the lancet device defines a plane P which is configured to contact (i.e., be positioned against) a user's skin. According to one non-limiting embodiment, the invention utilizes a planar front skin engaging surface or plane P. However, the instant embodiment may also utilize an inwardly curved and/or an outwardly curved (not shown) surface and/or plane P beyond which the lancet need can extend. The lancet needle LN itself can be arranged on the front end of the holding member 50 and can be a conventional lancet needle of the type, e.g., disclosed in U.S. Pat. No. 6,258,112, the entire disclosure of which is hereby expressly incorporated by reference. Alternatively, it can be of the type which is removable/replaceable, as is the case in many prior art lancet devices.

Figure 2:
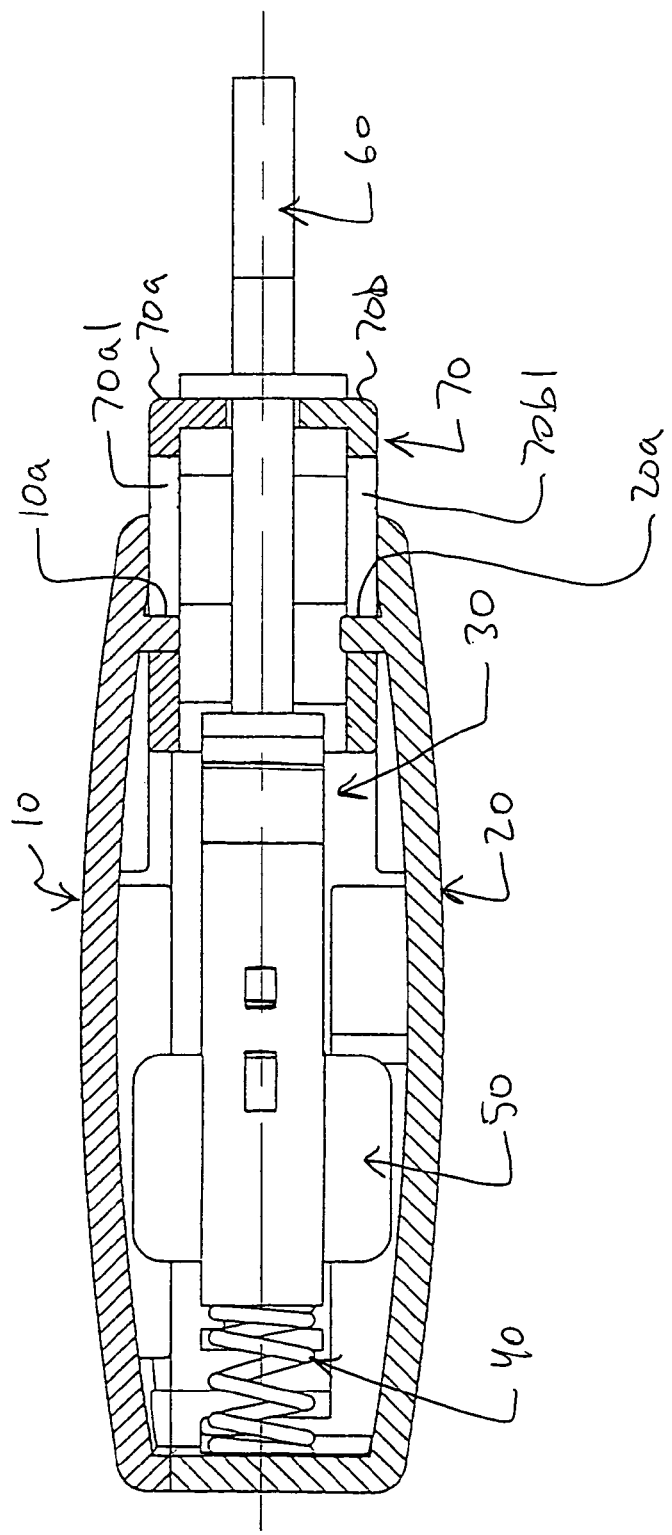
FIG. 2 shows a side cross-section view of the embodiment of FIG. 1. The spring, lancet mechanism and trigger prevention device are not shown in cross-section.

As can be seen in FIGS. 1 and 2, the lancet body is preferably ergonomically shaped, i.e., so as to be confortably gripped by the user. In this regard, the lancet body can have an elongated soap-shape. Of course, the invention contemplates other shapes for the lancet body provided that they result in a relatively inexpensive design and/or which are economical to produce. As explained above, the front end of the lancet device LD includes a skin engaging plane P. As will be explained in detail later on, the plane P is defined by outer front planar surfaces of both skin engaging member parts 70a and 70b. A lancet opening LO is arranged on the plane P and serves to allow the lancet needle LN to penetrate beyond the plane P (see FIGS. 8 and 9). The skin engaging member 70 is movably and/or slidably mounted to the lancet body. In the instant embodiment, the skin engaging member 70 is generally rectangular-shaped (see FIGS. 21-23). However, the invention contemplates other shapes for the skin engaging member 70 such as, e.g., circular, triangular, square, polygonal, etc. In the instant embodiment, the skin engaging member 70 is generally centrally mounted to a front area of the lancet body. However, the invention contemplates other locations and/or positions for the skin engaging member 70. The skin engaging member 70 is preferably slidably mounted in a front opening formed in the lancet body. The skin engaging member 70 can also optionally have a finger engaging (e.g. push button) portion PB (see FIGS. 26a-26e) that can be pushed into the lancet body. As will be explained in detail later on, the skin engaging member 70 functions, in combination with portions of the holding member 50, as a triggering device that it is capable of causing the automatic triggering of the lancet device LD (see FIGS. 6-9) when force is applied to the skin engaging member 70. The lancet device LD also preferably uses a system which prevents the skin engaging portion 70 from returning to a pre-triggered position (see FIG. 11).

The lancet body can preferably made transparent and/or translucent so that a user will clearly be able to identify when the device has already been used. Of course, the invention is not limited to a body design which is transparent and/or translucent.

As can be seen in FIGS. 2-11, a rear end of the holding member 50 is preferably coupled and/or fixedly secured to a front end 40a of a spring 40. The other end 40b of the spring 40 is coupled and/or fixedly secured to a rear inner wall of the lancet body. In this way, the spring 40 can be compressed so as to bias the holding member 50 towards an extended position and, once expanded, it can also bias the holding member 50 towards the retracted position. In this regard, the spring 40, which can be made of spring steel, and which can have the form of a helical coil compression spring, is arranged in a rear area of the holding member 50. In the position shown in FIGS. 2-5, the spring 40 is compressed and is ready to cause (and/or bias) the holding member 50 to move towards an extended position once the lancet device is triggered (see FIGS. 6 and 7). As FIGS. 6 and 7 demonstrate, this triggering is caused by sliding movement of the skin engaging member 70 into the lancet body (of course, this can occur only after the tab portion 60 is removed (see FIGS. 4 and 5)). This movement can generally be caused in two ways. In one way, a user grips the lancet device LD and forces (see force F in FIGS. 6 and 7) it against his or her skin in an area where a blood sample is to be taken, i.e., a finger, hand, arm, foot, etc. This movement forces the skin engaging member 70 to slide into the lancet body. Alternatively, the user can hold the lancet device LD in a generally fixed position and move a portion of the user's body towards the lancet device LD. The result is the same, the skin engaging member 70 is caused to move relative to the lancet body.

The skin engaging member 70 includes a significant portion that is arranged within the lancet body and is slidably mounted to the body parts 10, 20. To ensure that the skin engaging member 70 is slidably guided during this movement, inwardly extending projections 10a and 20a, which are fixed to and/or integrally formed with the lancet body, extend into recesses 70a1 and 70b1 arranged on the skin engaging member 70.

Figure 9:
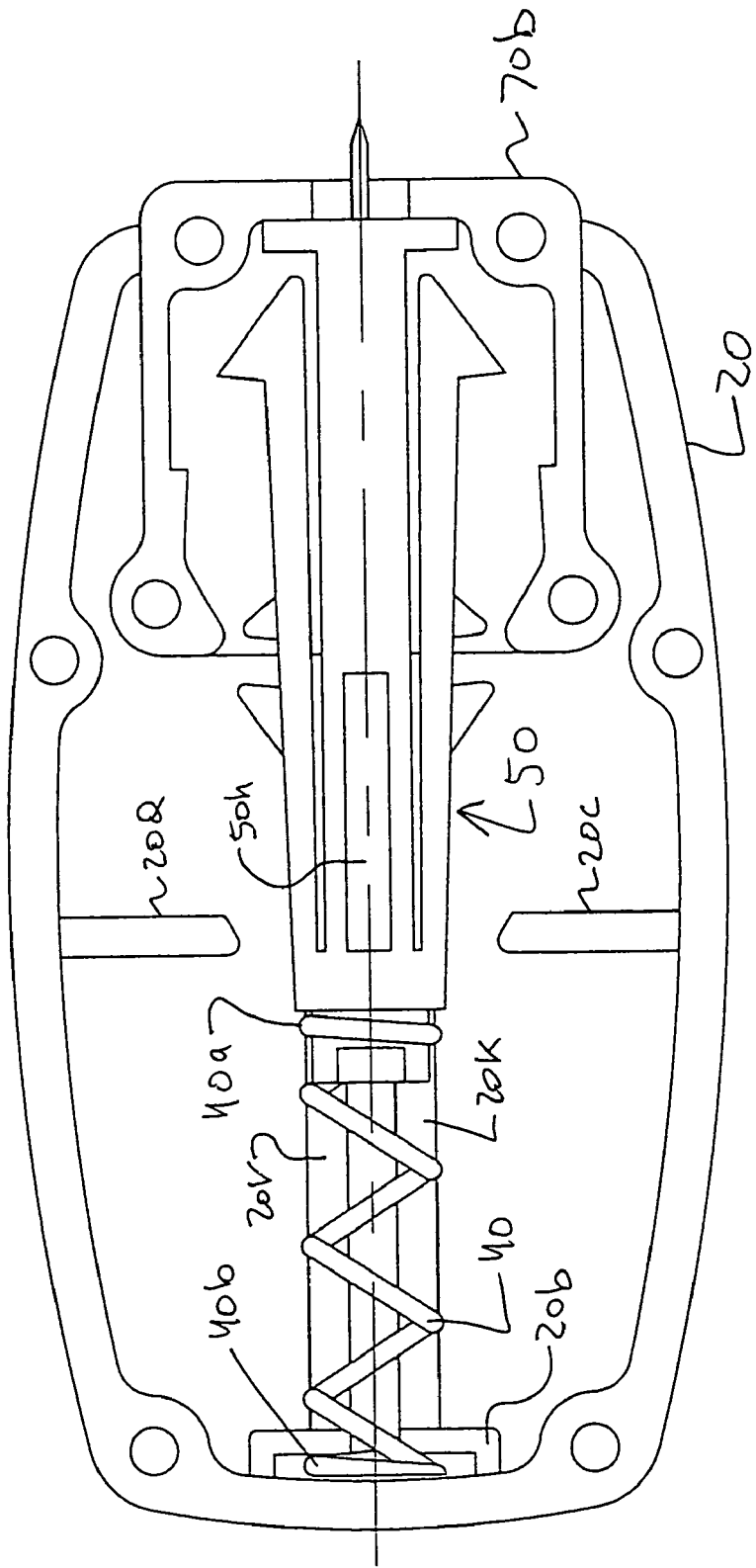
FIG. 9 shows a view similar to FIG. 7, but with the lancet holding member being in the position shown in FIG. 8.
Figure 10:
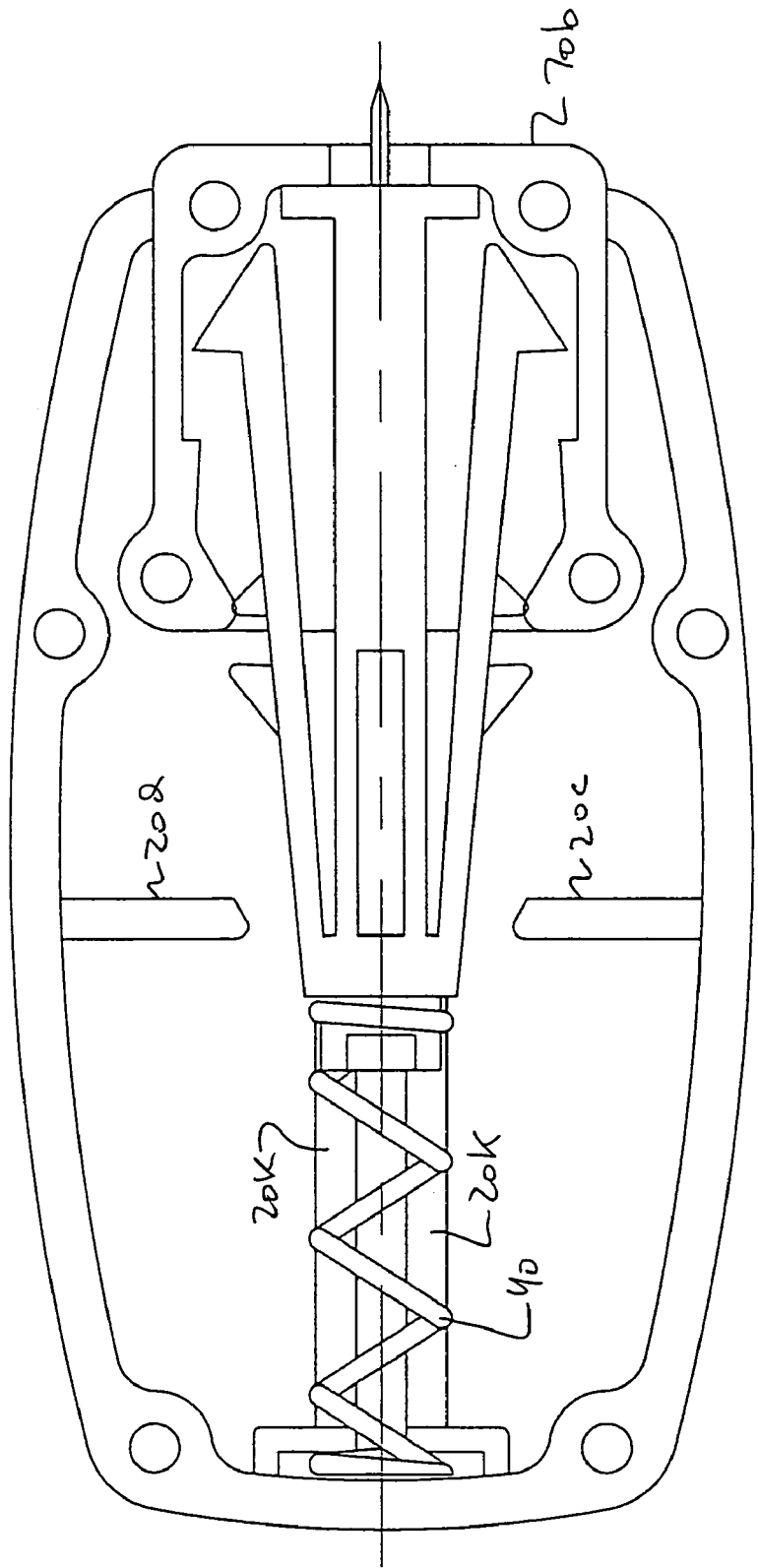
FIG. 10 shows a view similar to FIG. 9, but with the two arms of the lancet holding member have been deflected outwards until they generally engage inside surfaces and/or penetrate indentations of the skin engaging member.
Figure 11:
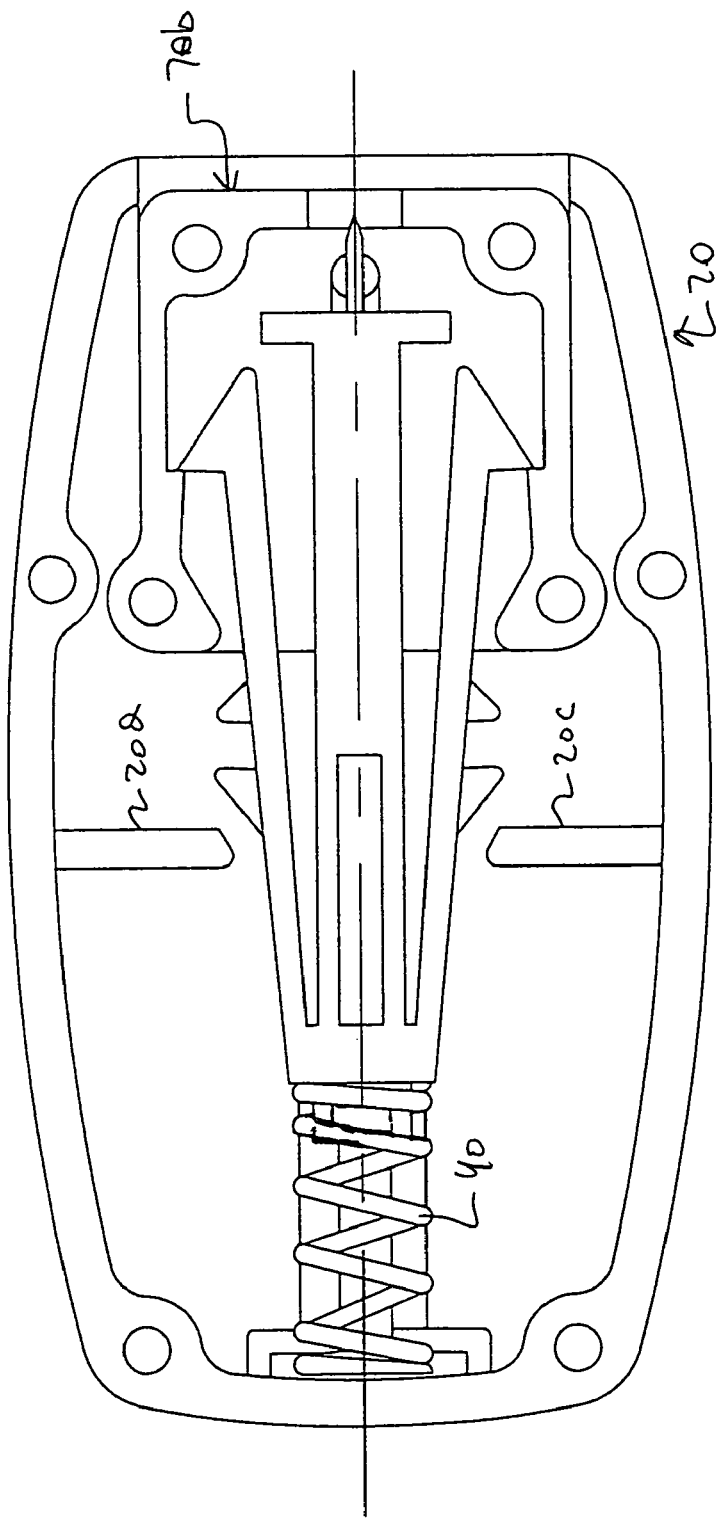
FIG. 11 shows a view similar to FIG. 10, but with the lancet holding member having been retracted to a certain extent under the action of the spring. The Figure also shows the projecting portions of the two arms of the lancet holding member having become engaged with internal shoulders of the skin engaging member. This engagement causes the skin engaging member to also retract or be pulled into the lancet body under the action of the spring. The lancet needle has also retracted back further behind the skin engaging surface or plane of the skin engaging member.

As can be seen in FIG. 9, the spring 40 has one end 40a which is secured to a rear end (and specifically portions 50c) of the holding member 50 and another end 40b which is secured to the lancet body or lower housing 20 via securing flanges 20b (see also FIG. 13). As with the projection 20a, the flanges 20b are preferably integrally formed with the housing part 20. In particular, the front end 40a of the spring 40 is axially retained between two oppositely arranged shoulders 50c and an another shoulder 50d (see FIGS. 24 and 25). The rear end 40b of the spring 40 is axially retained and/or connected to flanges 20b of the lancet body. The spring 40 also causes (and/or biases) the holding member 50 to move back towards an intermediate position (see FIG. 11) after the lancet needle LN and holding member 50 reach the extended position (see FIGS. 8 and 9). In this way, the lancet needle LN (and holding member 50) is automatically retracted after puncturing the skin of a user. In the embodiment shown in FIGS. 1-12, the lancet device LD is pre-loaded so that a user need only press and/or force the skin engaging member 70 against the skin to use the device. Once triggered, however, the user will be unable to use the lancet device LD again owing to the fact that this embodiment contains no mechanism for allowing the user to force or move the holding member 50 from the position shown in FIG. 11 to the armed, trigger-set, or retracted position shown in FIGS. 1-5. Moreover, because the spring 40 maintains the holding member 50 and the skin engaging member 70 in the position shown in FIG. 11, the lancet needle LN and the skin engaging member 70 are kept safely within the lancet body. By way of non-limiting example, the armed position of the holding member 50 shown in FIGS. 1-5 can be set when the lancet device LD is manufactured and/or assembled by compressing the spring 40 to a certain extent until the retaining projections 50e1 and 50e2, and 50f1 and 50f2 of the deflecting arms 50e and 50f engages with the retaining flanges 20c and 20d of the lancet body. As with the projection 20a and the flange 20b, the retaining flanges 20c and 20d can also be integrally formed with the housing part 20.

FIGS. 3, 5, 7 and 9-11 show views of the lower body part 20 and the various positions of the holding member 50. The lower body part 20 can preferably be made as one-piece structure by e.g., injection molding. In this regard, it is preferably made of a plastic or synthetic resin such as, e.g., ABS plastic. The lower body part 20 may also be made of ABS-757 and/or Metallic Silver and have a finish designated as SPI-A2. Of course, other materials and/or finishes may be utilized, without leaving the scope of the invention. Additionally, the lower body part 20 may have an overall length that is between approximately 2.5" and approximately 4", and is preferably approximately 33 mm. Although undesirable for reasons of cost, the lower body part 20 may even be made of a plurality of sections of parts which are joined together to form the complete lower body part 20, without leaving the scope of the invention.

With reference to FIGS. 13-16, it can be seen that the lower body part 20 preferably has a front straight edge 20e and two parallel support flanges 20f which slidably engage an outer surface of the skin engaging member 70. The lower body part 20 also preferably has an outwardly curved bottom surface 20g (see FIG. 14). This surface 20g extends from the rear wall 20h to the front edge 20e and may have a large radius of curvature on the order of approximately 98 mm (measured in FIG. 15). This surface 20g also extends from side walls 20i and 20j and may have a large radius of curvature on the order of approximately 48 mm (measured in FIG. 14). Alternatively, the surface 20g may be essentially straight and/or planar, and may even be inwardly curved. The lower body part 20 additionally preferably includes two plate-like projections or retaining flanges 20c and 20d which are generally centrally disposed relative to wall 20h and edge 20e. The side walls 20i and 20j extend from the rear wall 20h to the front edge 20e and may each have a large radius of curvature on the order of approximately 60 mm (measured across FIG. 13). The purpose of the retaining flanges 20c and 20d is to help hold and/or retain the holding member 50 in the retracted position as discussed above. The lower body part 20 additionally preferably includes two elongated generally parallel projecting rails 20k which are generally centrally disposed relative to side walls 20i and 20j and which act to guide the holding member 50 along a generally linear path as it moves from the retracted position, to the extended position, and back to an intermediate position. These rails 20k define a space therebetween which receives therein the lower guiding flange 50h of the holding member 50. The guiding slidable engagement between the flange 50h and the rails 20k ensure that the holding member 50 moves back and forth in a non-rotatable manner. In this regard, the projecting rails 20k are spaced apart by a distance which is generally similar, and/or slightly larger (to provide the required clearance), than a width or thickness of the guiding flange 50h. Two L-shaped projecting walls 20b extend inwardly from the wall 20h of the lower body 20. These walls 20b retain end 40b of the spring 40. In order to allow the skin engaging member 70 move freely (without also rotating) within the lancet device LD, a projection 20a extends inwardly and is sized to slide within a recess 70b1 of the lower part 70b of the skin engaging member 70. The recess 70b1 (see FIGS. 21-23) is preferably slightly larger (to provide the required clearance) than the projection 20a to allow the skin engaging member 70 to be guided and to move and/or slide freely within the lancet device LD. In this regard, the lower housing part 20 provides a generally planar support surface (formed by the surface of 201 and upper surface of projections 20f) for linearly guiding and/or slidably engaging an outer surface of the skin engaging member 70. The lower body part 20 also preferably includes openings 20m which are sized to receive therein connecting projections or pins 10i of the lancet body cover 10.

By way of non-limiting example, the openings 20m can have a diameter of approximately 1.2 mm. The flanges 20c and 20d may have a thickness of approximately 1 mm. The distance to an outer surface of the flanges 20c and 20d from an outer surface of wall 20h can be approximately 14.5 mm. An overall width (measured across FIG. 13) between walls 20i and 20j can be approximately 18 mm. An overall thickness or height (measured across FIG. 2) between walls 20g and 10j of the lancet device LD can be approximately 12 mm. The spacing distance between rails 20k can be approximately 1.2 mm and the spacing distance between projecting portions 20f can be approximately 5 mm. An overall width (measured across FIG. 13) between outer surfaces of projections 20f can be approximately 7 mm and an overall width (measured across FIG. 13) between outer surfaces of projections 20k can be approximately 3.2 mm. The inner ends of flanges 20c and 20d may have angled end surfaces which are angled at approximately 60 degrees relative to the opposite parallel surfaces of the flanges 20c and 20d. With exception of certain areas, such as e.g., the corners, the walls 20h, 20i, 20j and 20g may generally have thicknesses of approximately 1.2 mm. The projection 20a may have a diameter of approximately 1.5 mm and may extend inwardly relative to surface 201 by approximately 1.2 mm. The surface 201 may have a width (measured up and down in FIG. 13) of approximately 11 mm. A spacing between inner edges of the flanges 20c and 20d can be approximately 6.25 mm.

The upper body part or lancet body cover 10 can preferably be made as one-piece structure by e.g., injection molding. In this regard, it is preferably made of a plastic or synthetic resin such as, e.g., ABS plastic. The cover part 10 may also be made of ABS-757 and/or Metallic Silver and have a finish designated as SPI-A2. Of course, other materials and/or finishes may be utilized, without leaving the scope of the invention. Additionally, the cover part 10 may have an overall length that is between approximately 2.5" and approximately 4", and is preferably approximately 33 mm. Although undesirable for reasons of cost, the upper body part 10 may even be made of a plurality of sections of parts which are joined together to form the complete upper body part 10, without leaving the scope of the invention.

With reference to FIGS. 17-20, it can be seen that the cover part 10 preferably has a front straight edge 10g and two generally parallel support flanges 10b which slidably engage an outer surface of the skin engaging member 70. The cover part 10 also preferably has an outwardly curved upper surface 10j (see FIG. 18). This surface 10j extends from the rear wall 10d to the front edge 10g and may have a large radius of curvature on the order of approximately 98 mm (measured in FIG. 19). This surface 10j also extends from side walls 10e and 10f and may have a large radius of curvature on the order of approximately 48 mm (measured in FIG. 18). Alternatively, the surface 10j may be essentially straight and/or planar, and may even be curved inwardly. The side walls 10e and 10f extend from the rear wall 10d to the front edge 10g and may each have a large radius of curvature on the order of approximately 60 mm (measured across FIG. 17). The cover part 10 additionally preferably includes two generally parallel elongated projecting rails 10c which are generally centrally disposed relative to side walls 10e and 10f and which act to guide the holding member 50 along a generally linear path as it moves from the extended position to the retracted position and vice versa. These rails 10c define a space therebetween which receives therein the upper guiding flange 50h of the holding member 50. The guiding slidable engagement between the upper flange 50h and the rails 10c ensure that the holding member 50 moves back and forth in a non-rotatable manner. In this regard, the projecting rails 10c are spaced apart by a distance which is generally similar, and slightly larger (to provide the required clearance), than a width or thickness of the upper guiding flange 50h. In order to allow the skin engaging member 70 move freely (without also rotating) within the lancet device LD, a projection 10a extends inwardly and is sized to slide within recess 70a1 of the upper part 70a of the skin engaging member 70. The recess 70a1 (see FIGS. 21-23) is preferably slightly larger than the projection 10a to allow the skin engaging member 70 to be guided and to move and/or slide freely within the lancet device LD. In this regard, the cover part 10 provides a generally planar support surface (formed by the surface of 10h and outer surfaces of projections 10b) for linearly guiding and/or slidably engaging an outer surface of the skin engaging member 70. The cover part 10 also preferably includes pins 10i which are sized to extend into and connect with connecting openings 20m of the lower housing 20.

By way of non-limiting example, the pins 10i can have a diameter of approximately 1.2 mm. An overall width (measured across FIG. 17) between walls 10f and 10e can be approximately 18 mm. An overall width (measured across FIG. 2) between walls 20g and 10j of the lancet device LD can be approximately 12 mm. The spacing distance between rails 10c can be approximately 1.2 mm and the spacing distance between projecting portions 10b can be approximately 5 mm. An overall width (measured across FIG. 17) between outer surfaces of projections 10b can be approximately 7 mm and an overall width (measured across FIG. 17) between outer surfaces of projections 10c can be approximately 3.2 mm. Walls 10d, 10e, 10f, and 10j may thicknesses of approximately 1.2 mm. The projection 10a may have a diameter of approximately 1.5 mm and may extend inwardly relative to surface 10h by approximately 1.0 mm. The surface 10h may have a width (measured up and down in FIG. 17) of approximately 11 mm.

As explained above, the lancet device LD utilizes a retractable skin engaging member 70 to cause the triggering of the lancet device LD. The skin engaging member 70 can preferably be a two-piece arrangement that includes an upper part 70a and a lower part 70b (see FIGS. 21-23). The skin engaging member 70 is movably and/or slidably mounted to the lancet body via a rectangular-shaped opening formed by the front ends of the housing parts 10 and 20. The skin engaging member 70 is generally linearly guided within this opening via projections 10a, 20a and recesses 70a1 and 70b1, and is at least partially disposed in the opening (see e.g., FIG. 1). Of course, the skin engaging member 70 can be mounted within the lancet body in any desired manner provided that it functions properly. To ensure that the skin engaging portion 70 and the holding member 50 cannot be moved accidentally, and to ensure that these parts are axially retained to lancet body, a removable tab portion 60 is removably connected to the front end of the holding member 50. As is evident from, e.g., FIG. 3, when the tab portion 60 is coupled to the holding member 50, the flange 60b prevents the skin engaging member 70 from moving away from the lancet body and into the lancet body. Thus, if one pushes the tab portion 60 into the lancet body, neither the tab portion 60, nor the skin engaging member 70, and nor the holding member 50 will move owing to the fact that projections 50e1, 50e2 and 50f1, 50f2 are engaged with flanges 20d and 20c. Similarly, if one pulls the tab portion 60 away from the lancet body, neither the tab portion 60, nor the skin engaging member 70, and nor the holding member 50 will move owing to the fact that projections 50e1, 50e2 and 50f1, 50f2 are engaged with flanges 20d and 20c. Of course, if a user pulls with sufficient force to cause separation of the tab portion 60 from the holding member 50 (see FIGS. 4 and 5), the tab portion 60 will be removed from the holding member 50, but the holding member 50 and skin engaging member 70 will not move as a result. Thus, the tab portion 60 serves as a safety and/or trigger prevention system. Of course, the invention contemplates other mechanisms for preventing the accidental triggering of the lancet device LD and also contemplates a lancet device LD which does not utilize such a system.

FIGS. 21a-23d show various views of the two-piece skin engaging member 70. The skin engaging member 70 is preferably be made as two-piece structure by e.g., injection molding, each piece 70a, 70b. Alternatively, the skin engaging member 70 can be made as a one-piece member. The skin engaging member 70, or parts 70a, 70b, are preferably made of a plastic or synthetic resin such as, e.g., ABS plastic. The skin engaging member 70 may also be made of ABS-757 or ABS-Dark Blue and have a finish designated as MT-11040. Additionally, the skin engaging member 70 may have an overall length (measured across FIG. 21a or 21b) that is approximately 12 mm and an overall width (measured up and down in FIGS. 21a or 21b) of approximately 12.6 mm. Of course, other materials and/or finishes and/or sizes may be utilized, without leaving the scope of the invention.

By way of non-limiting example, the connecting pins Pi and recesses Re of the parts 70a and 70b can have a diameter of approximately 1.2 mm. A width of the slots 70a1 and 70b1 can be approximately 1.5 mm and a length of the slots 70a1 and 70b1 (from centerline to centerline) can be approximately 5.8 mm. The spacing distance between rounded ends 70a7 and between rounded ends 70b7 can be approximately 7 mm. The angled surfaces 70a6 and 70b6 can have an angle of approximately 120 degrees relative to the edge of the parts 70a and 70b opposite the surfaces 70a2 and 70b2 defining the plane P. The parts 70a and 70b may have wall thickness of approximately 1 mm, except for the thickened corner areas and the thinner wall areas defining the indented surfaces 70a4 and 70b4. An inner spacing distance between surfaces 70a4 and 70b4 may be approximately 9.6 mm. The centrally disposed lancet needle opening, defined by half-round indentations 70a3 and 70b3, can be approximately 2 mm in diameter. A distance between the surfaces 70a2 and 70b2, defining the plane P, and shoulders 70a5 and 70b5 can be approximately 8 mm. A vertical distance between the center-lines of the pin Pi and recess Re adjacent the surfaces defining the plane P can be approximately 8.2 mm, and a vertical distance between the center-lines of the pin Pi and recess Re adjacent the opposite surfaces near rounded ends 70a6 and 70b6 can be approximately 10.2 mm. A horizontal distance between the center-lines of the pins Pi and recesses Re adjacent the surfaces defining the plane P and the opposite surfaces near rounded ends 70a6 and 70b6 can be approximately 9.4 mm. A horizontal distance between the centerline of the first rounded portion of slots 70a1 and 70b1 and the straight surfaces near the rounded ends 70a7 and 70b7 can be approximately 4 mm.

Figure 24:
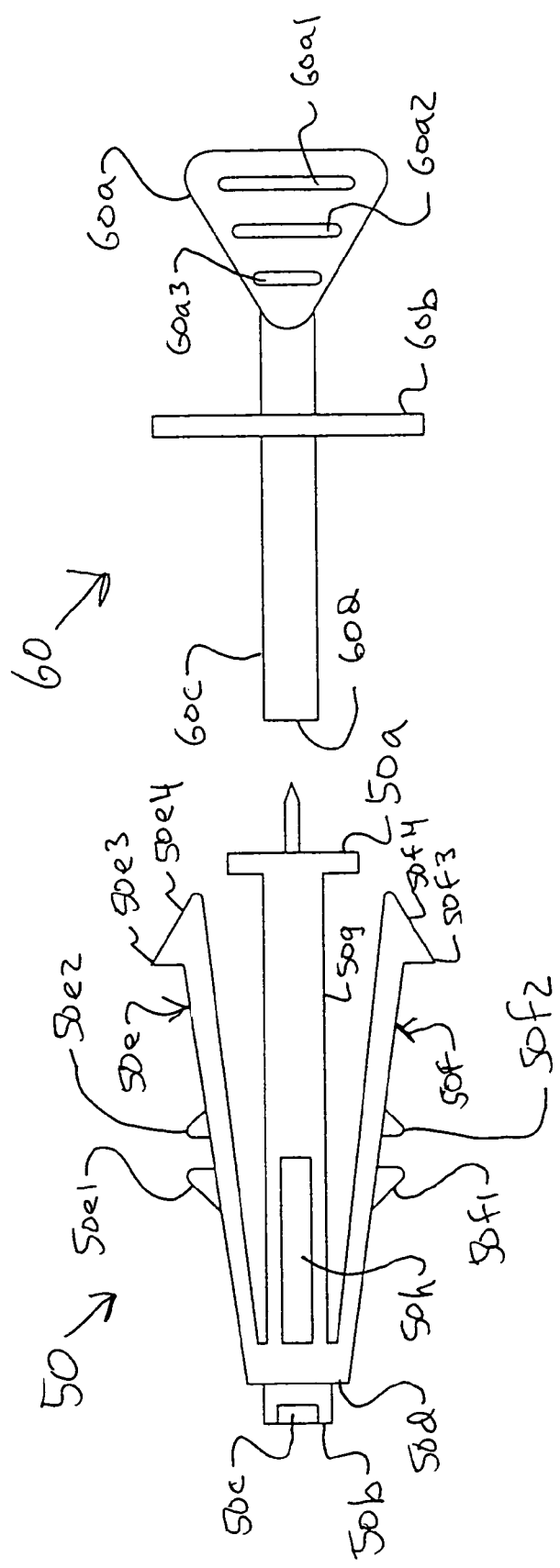
FIG. 24 shows a top view of the two-piece lancet mechanism used in the embodiment of FIGS. 1-12. The tab portion of the lancet mechanism is shown removed from the lancet holding member portion.

FIGS. 24-25f show various views of the two-piece lancet mechanism 30, as well as the parts 50 and 60 which make up the two-piece lancet mechanism 30. The lancet mechanism 30 includes a holding member 50, which can preferably be made as one-piece structure by e.g., injection molding, and a tab portion 60, which can preferably be made as one-piece structure by e.g., injection molding. In this regard, parts 50 and 60 are preferably made of a plastic or synthetic resin such as, e.g., ABS plastic or Delrin plastic. The holding member 50 and tab portion 60 may also be made of ABS-757 or Delrin-Natural and have a finish designated as SPI-C1. Of course, other materials and/or finishes may be utilized, without leaving the scope of the invention. Additionally, the lancet mechanism 30 may have an overall assembled length (measured across FIGS. 25b and 25c) that is approximately 43 mm. Moreover, the holding member 50 and tab portion 60 may each be made of a plurality of sections of parts which are joined together to form the complete lancet mechanism 30, without leaving the scope of the invention.

The holding member 50 preferably has a body portion 50g that is generally rectangular-shaped cross-section and which may have a thickness (measured up and down in FIG. 24) of approximately 2.2 mm and a thickness (measured up and down in FIG. 25b) of approximately 4.5 mm. Of course, the invention also contemplates other cross-sectional shapes for the body portion 50g of the holding member 50 such as square, oval, polygonal, etc. The body 50g has a front shoulder end which is sized and configured to securely retain and receive the lancet needle LN, which may be a conventional lancet needle. The holding member 50 also includes a rear cylindrical section 50b (or other shaped section) which may have a diameter of approximately 2.5 mm. This rear section 50b includes two oppositely arranged projections 50c (see FIG. 25f) which are sized and shaped to securely retain the front portion 40a of the spring 40. The projections 50c may have a width (measured across FIG. 25f) of approximately 1.5 mm and a thickness (measured across FIG. 25b) of approximately 0.7 mm. A distance between shoulder 50d and end 50b can be approximately 1.5 mm. The front end of the body portion 50g includes an enlarged square shaped shoulder (see FIG. 25e) which defines the contact surface 50a. The width and height of the square-shaped contact surface can be approximately 4.8 mm by 4.8 mm.

As can be seen in FIGS. 24 and 25, two integrally formed oppositely arranged deflecting members 50e and 50f preferably extend from a rear area of the holding member 50. These deflecting members 50e and 50f each have a half-arrow shaped end which includes angled surfaces 50e4 and 50f4 and engaging shoulder ends 50e3 and 50f3. Each deflecting member or arm 50e, 50f also includes two retaining projections 50e1, 50e2 and 50f1, 50f2. As explained above, these projections 50e1, 50e2 and 50f1, 50f2 engage two retaining flanges 20c and 20d of the lower housing part 20 when the holding member 50 is in the trigger set position. The angled surfaces of the projections 50e1, 50e2 and 50f1, 50f2 can be angled at approximately 45 degrees relative to the straight or planar parallel surfaces defining the space between the projections 50e1 and 50e2, and projections 50f1 and 50f2. The angle defined between angled surfaces of projections 50e1 and 50e2 can be twice this angle or approximately 90 degrees, and the angle defined between angled surfaces of projections 50f1 and 50f2 can be twice this angle or approximately 90 degrees.

The spacing distance between the straight or planar parallel surfaces defining the space between the projections 50e1 and 50e2 and between projections 50f1 and 50f2 can be approximately 1.2 mm. A spacing width (measured up and down in FIG. 24) between ends 50e3 and 50f3 can be approximately 10.5 mm and a spacing width (measured up and down in FIG. 24) between ends of projections 51e1, 50e2 and 50f1, 50f2 can be approximately 8.1 mm. Two integrally formed projecting flanges 50h also preferably extend from a rear area of the holding member 50. As explained above, these projecting flanges 50h are sized to slide within flanges 10c and 20k of the lancet body so as to guide the linear movement of the holding member 50 within the lancet body and prevent rotation of the holding member 50 during such movement. The oppositely arranged symmetric flanges 50h are approximately 7 mm long (measured horizontally in FIGS. 25b and 25c) and extend away from body portion 50g by approximately 2 mm. A distance between the rear surface 50b and the forward edge of the flanges 50h can be approximately 10 mm.

The tab portion 60, which functions a trigger prevention mechanism, preferably has a body portion 60c that is generally cylindrical and which may have a diameter of approximately 2 mm. Of course, the invention also contemplates other cross-sectional shapes for the body portion 60c of the tab portion 60 such as square, oval, polygonal, etc. The body 60c has a rear end 60d which is sized and configured to securely cover the lancet needle LN. Although not shown, a breakable connection can be provided between the rear end 60d and the surface 50a of the holding member 50. The tab portion 60 also includes a head portion or gripping part 60a which is generally triangular in shape (of course it could have any desired shape). To facilitate gripping, a plurality of indentations 60a1-60a3 are provided on opposite sides of the head 60a. Of course, these indentations could be replaced with projections and/or another type of high-friction surface to facilitate gripping by the user. An oval-shaped flange 60b (of course it could have any other desired shape) is arranged between the head 60a and end 60d. The up and down overall height of the oval flange 60b (see FIG. 25a) can be approximately 5.5 mm and the left to right width of the oval flange 60 can be approximately 10 mm. The flange 60b is positioned so as to contact and/or abut the plane P of the skin engaging member 70 when the skin engaging member 70 and the holding member 50 are in the trigger-set position (see e.g., FIG. 3), and when the end 60d of the tab portion 60 contacts the stop surface 50a of the holding member 50. In this regard, the distance between the surface 60d and the start of the flange 60b can be approximately 10.7 mm. The thickness of the flange 60b can be approximately 0.8 mm.

Figure 3:
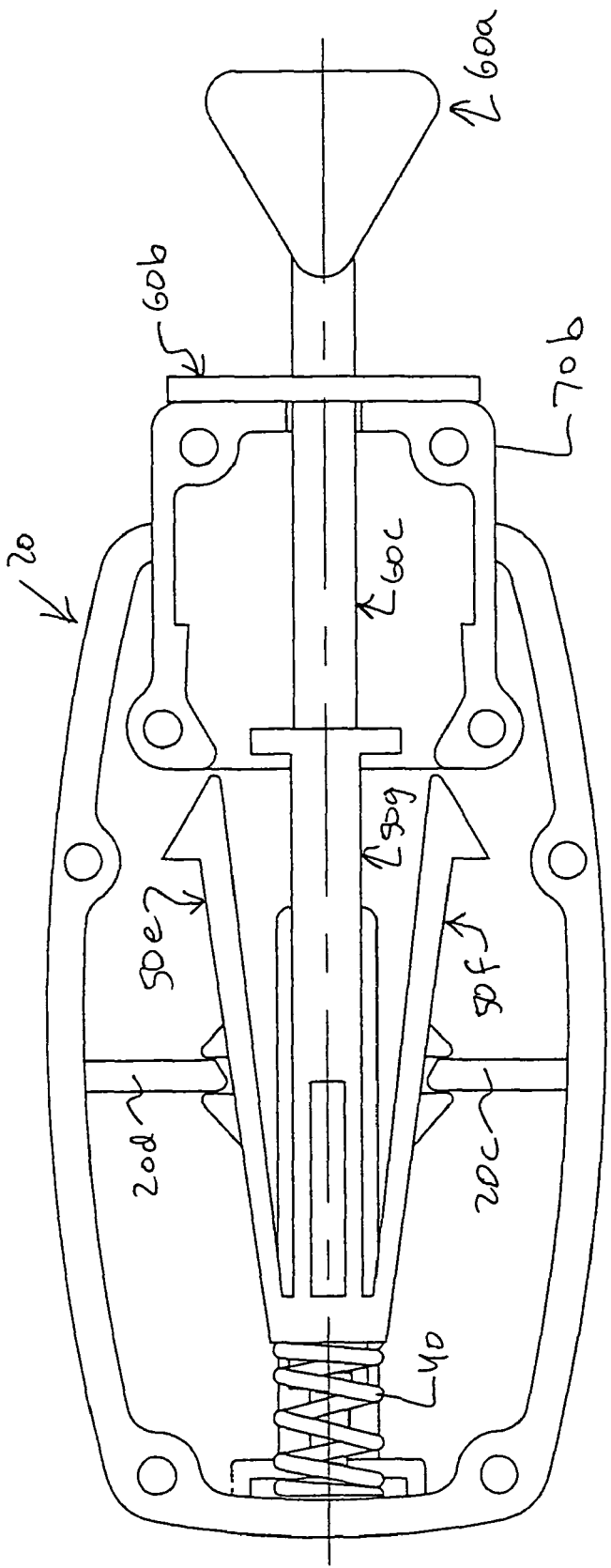
FIG. 3 shows a top view of the embodiment shown in FIG. 1, but with the body cover removed and the upper portion of the skin engaging member removed thereby exposing the inside workings of the lancet device. The lancet mechanism is in a loaded (retracted) position and the spring is compressed.
Figure 4:
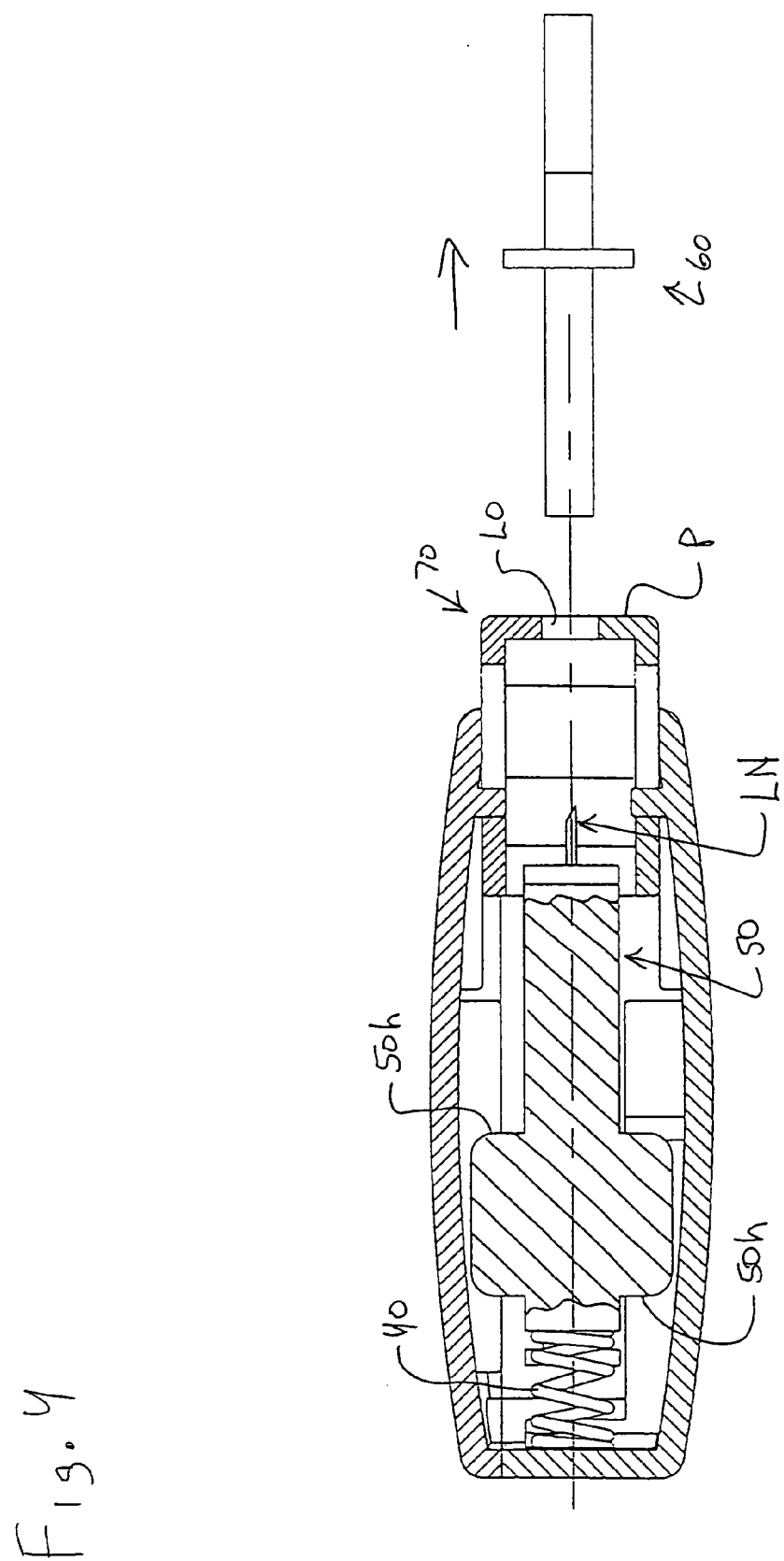
FIG. 4 shows a cross-section view similar to FIG. 2, but with the tab portion or trigger prevention device of the lancet mechanism being removed from the lancet holder portion of the lancet mechanism.
Figure 5:
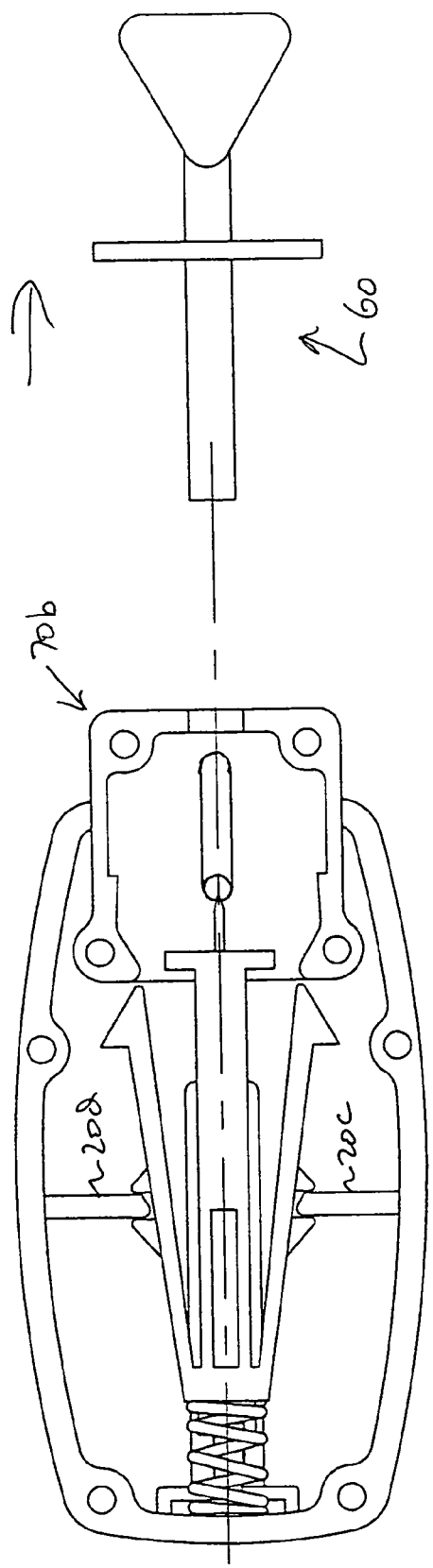
FIG. 5 shows a view similar to FIG. 3, but with the tab portion of the lancet mechanism being removed from the lancet holder portion as in FIG. 4.
Figure 6:
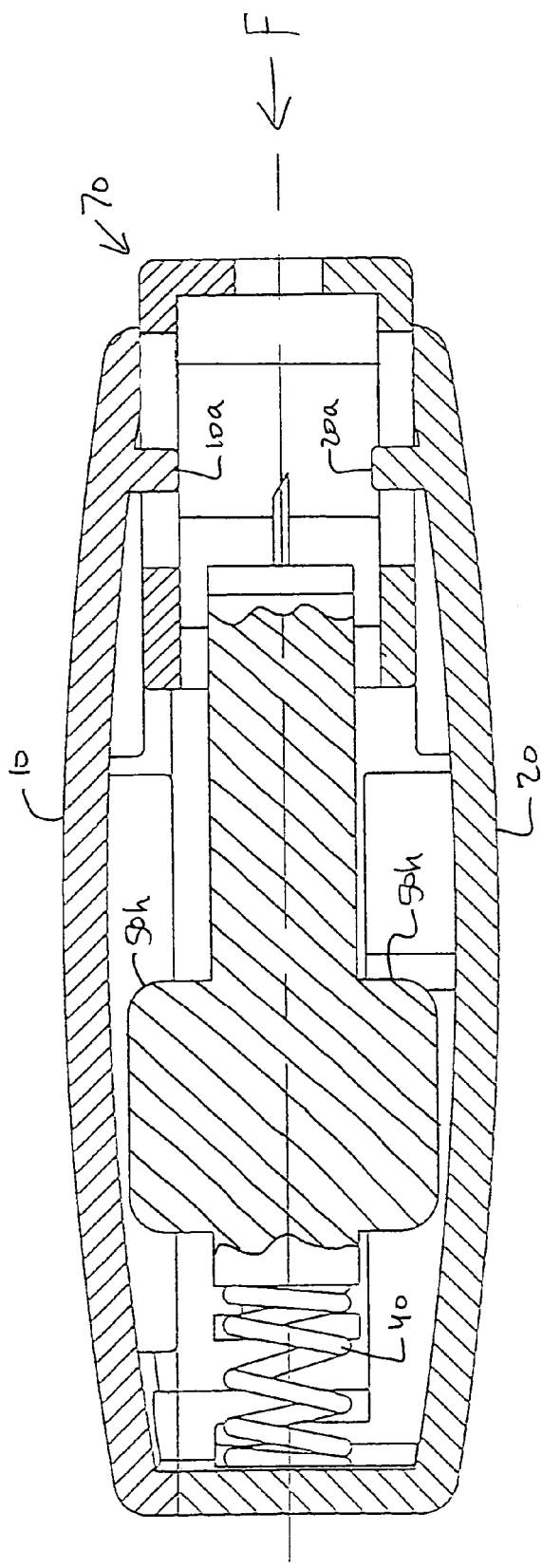
FIG. 6 shows a cross-section view similar to FIG. 4, but with the skin engaging head being moved into the lancet body to a partially retracted position. This can occur, e.g., when the lancet device is pressed against a user's skin.
Figure 7:
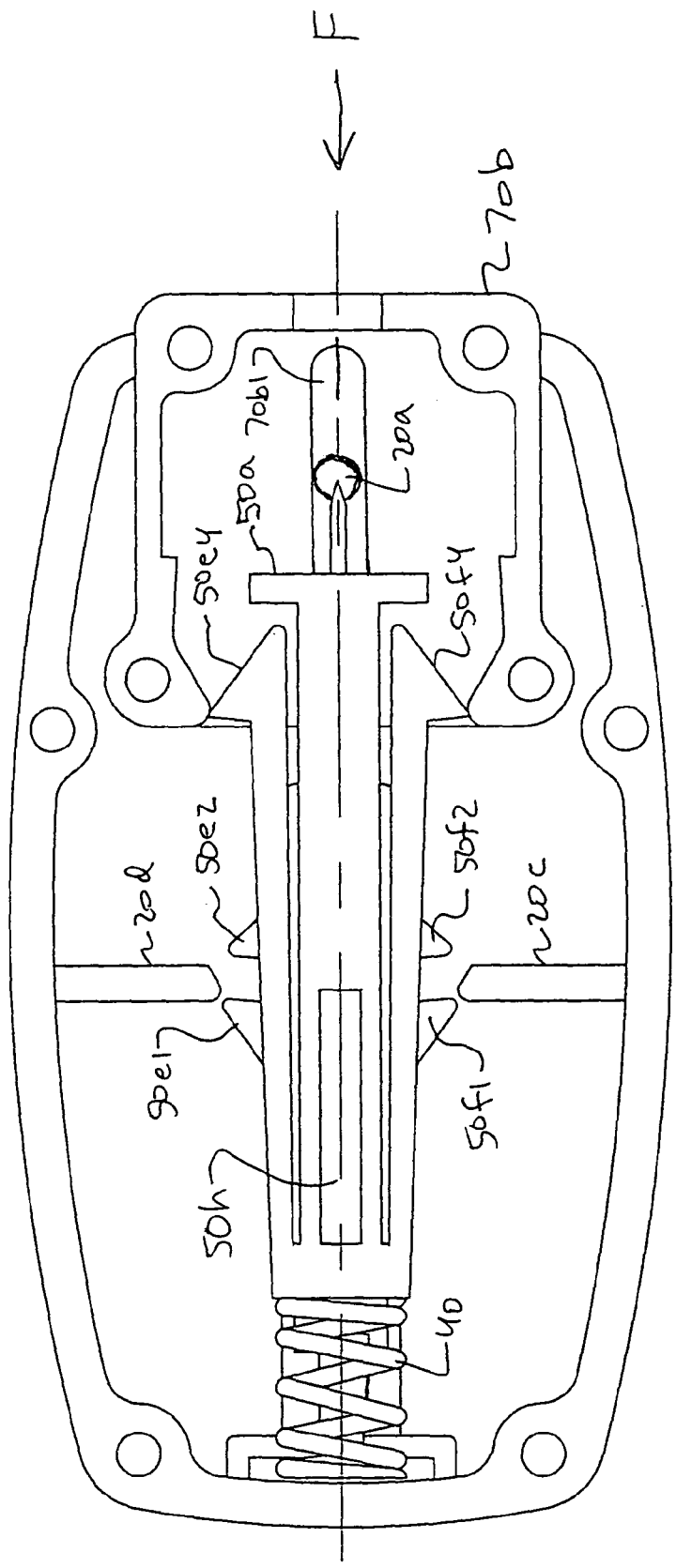
FIG. 7 shows a view similar to FIG. 3, but with the skin engaging head being moved to a partially retracted position as shown in FIG. 6. In this position, the two arms of the lancet holder portion or holding member have been deflected inwards by movement of the skin engaging head or member into the lancet body. The two arms have also become disengaged from two retaining flanges of the lancet body and the holding member is ready to be moved forward to the extended position under the biasing action of the spring.
Figure 8:
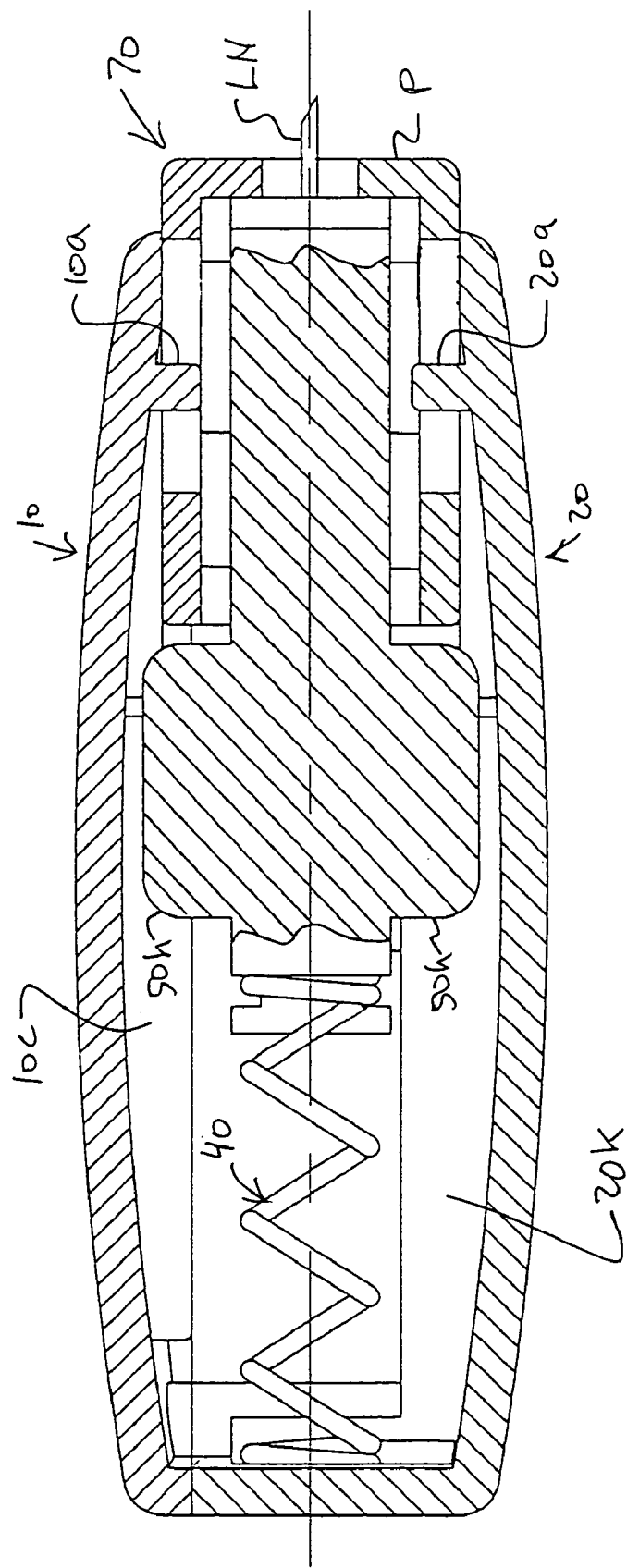
FIG. 8 shows a cross-section view similar to FIG. 6. The holding member has now moved forward under the action of the spring and the lancet needle has passed through the lancet opening so as to pierce or penetrate the skin of a user.

The operation of the device will now be explained. FIGS. 1-3 shows the lancet device LD with the lancet mechanism 30 and the skin engaging member 70 in the loaded trigger-set position. The holding member 50 and skin engaging member 70 retains the loaded position of FIGS. 1-3 as a result of the installation of the tab portion 60 as explained above. On the other hand, FIGS. 4 and 5 shows what happens when the tab portion 60 is removed, i.e., the lancet needle LN is now exposed and the lancet device LD can then be used and/or triggered. FIGS. 6 and 7 show what happens when the skin engaging member 70 is then forced to move into the lancet body, i.e., movement of the skin engaging member 70 inwards causes inward deflection of the two arms 50e and 50f owing to the sliding engagement between angled surfaces 50e4 and 50f4 and the rounded corners 70a7 and 70b7. This inward deflection of the arms 50e and 50f causes the projections 50e1, 50e2 and 50f1, 50f2 to disengage from the retaining flanges 20d and 20c. This, in turn, instantly allows the spring 40 to expand and cause the holding member 50 to move rapidly to the extended position (see FIGS. 8 and 9). The lancet needle LN is then free to penetrate the skin of a user in the position shown in FIGS. 9 and 10. The depth of penetration of the lancet needle LN is controlled by contact between surface 50a and surfaces 70a8 and 70b8. At this point, the arms 50e and 50f are again free to deflect outwardly owing to their inherent spring-like arrangement, i.e., the memory of their original relaxed position shown in FIG. 24. The projecting portions 50e3 and 50f3 then extend into indentations 70a4 and 70b4. At essentially the same time, the spring 40 causes the holding member 50 to retract until it reaches the relaxed position shown in FIG. 11. This retraction of the holding member 50 causes the projecting portions 50e3 and 50f3 to engage with shoulders 70a5 and 70b5 of the skin engaging member 70. As a result, when the holding member 50 retracts further into the lancet device LD, it will grip the skin engaging member 70 and pull it further into the lancet device LD until it reaches the position generally shown in FIG. 11.

Figure 12:
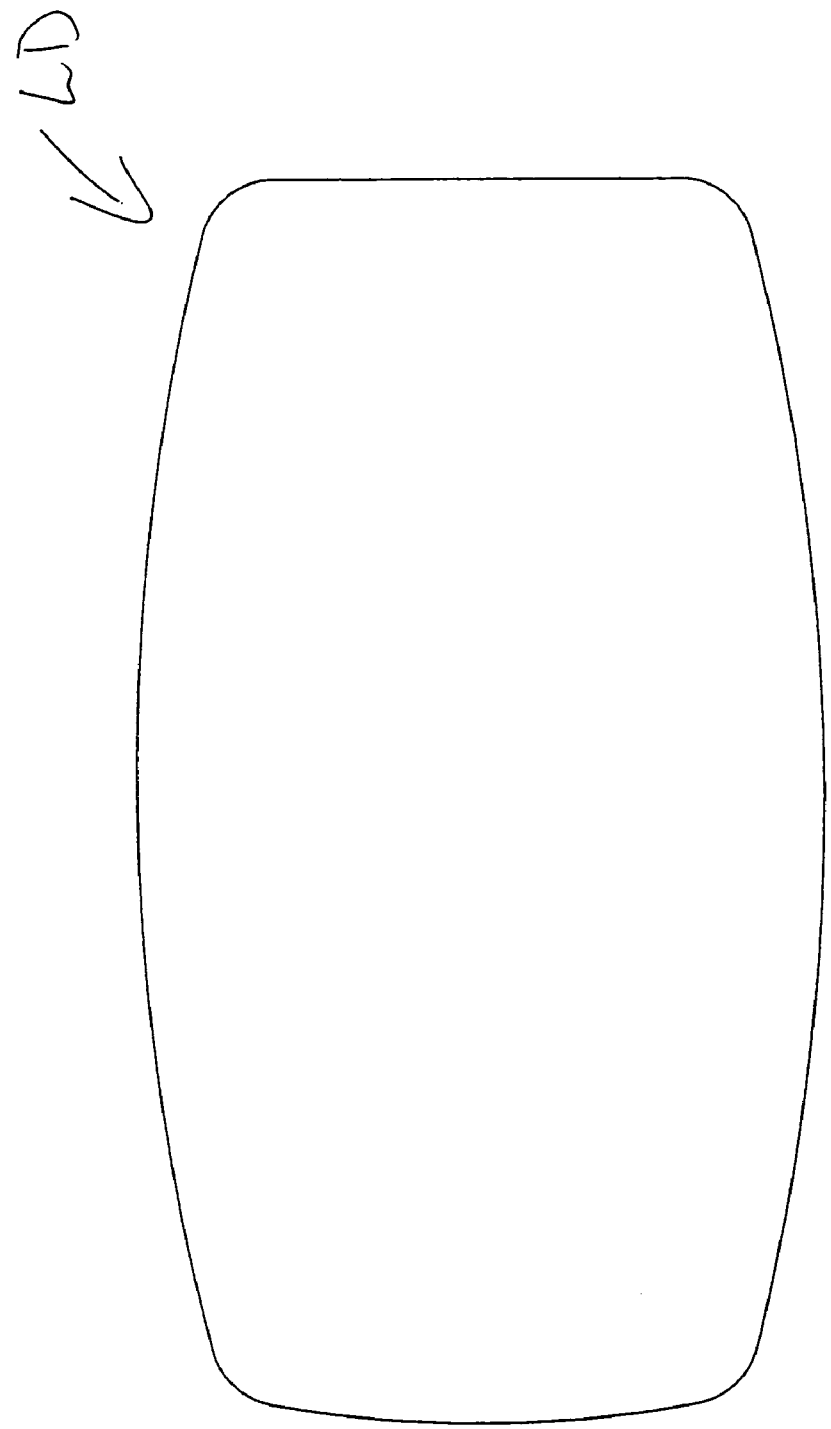
FIG. 12 shows a top view of the embodiment shown in FIGS. 1-11 in the used and/or trigger position of FIG. 11. The Figure illustrates how the skin engaging member and lancet needle has been retracted into the lancet body so as to be beyond view and exposure.
Figure 16:
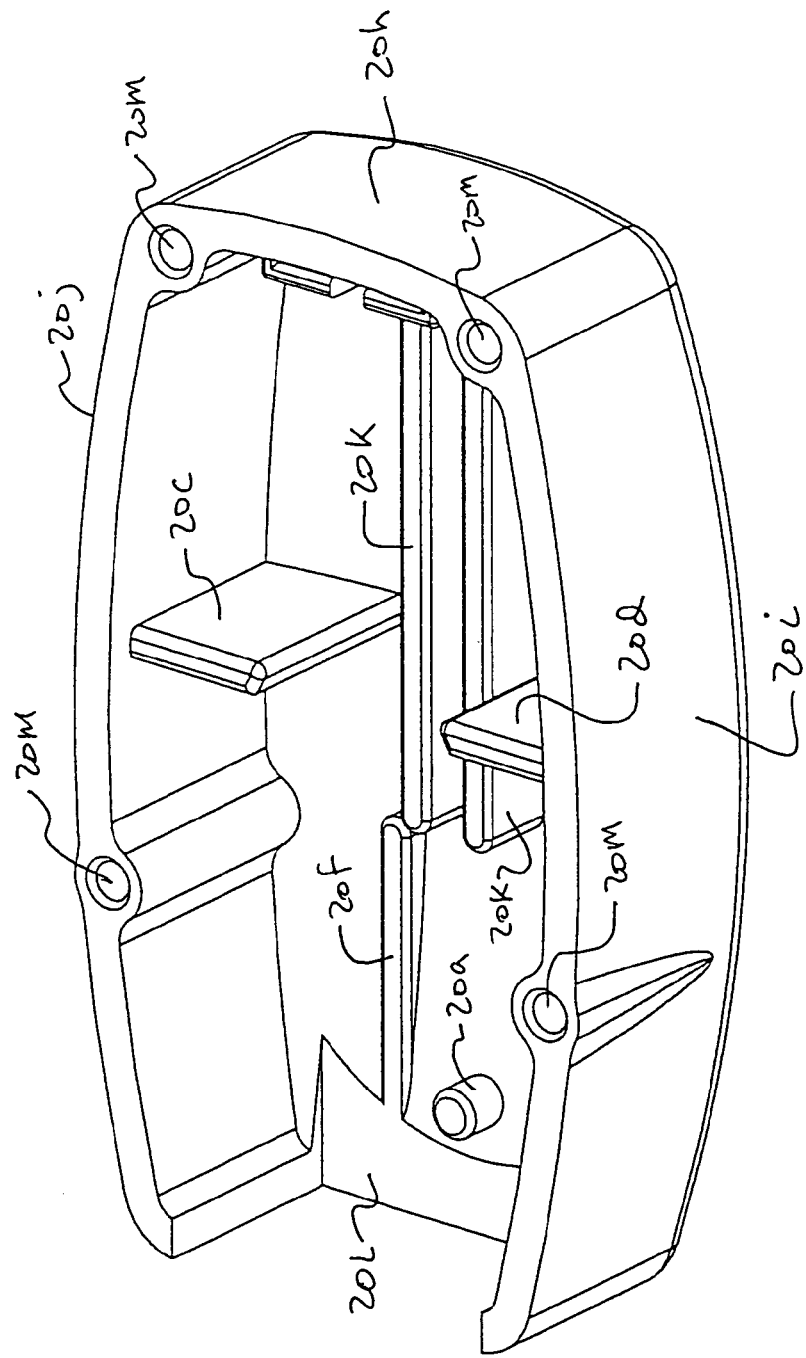
FIG. 16 shows a perspective view of the lancet body member of FIG. 13.
Figure 18:
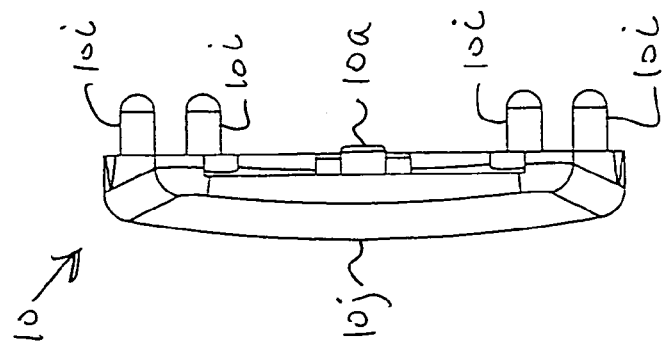
FIG. 18 shows a front end view of FIG. 17.
Figure 17:
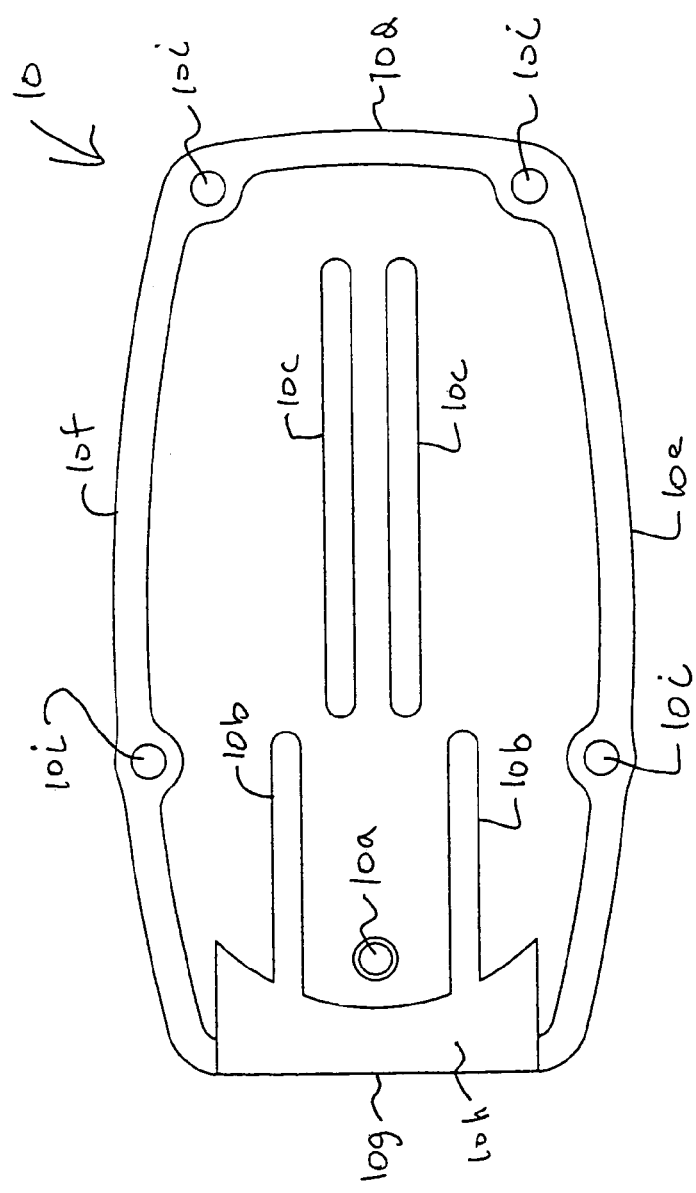
FIG. 17 shows an inside view of the lancet body cover used in the embodiment shown in FIGS. 1-12.
Figure 20:
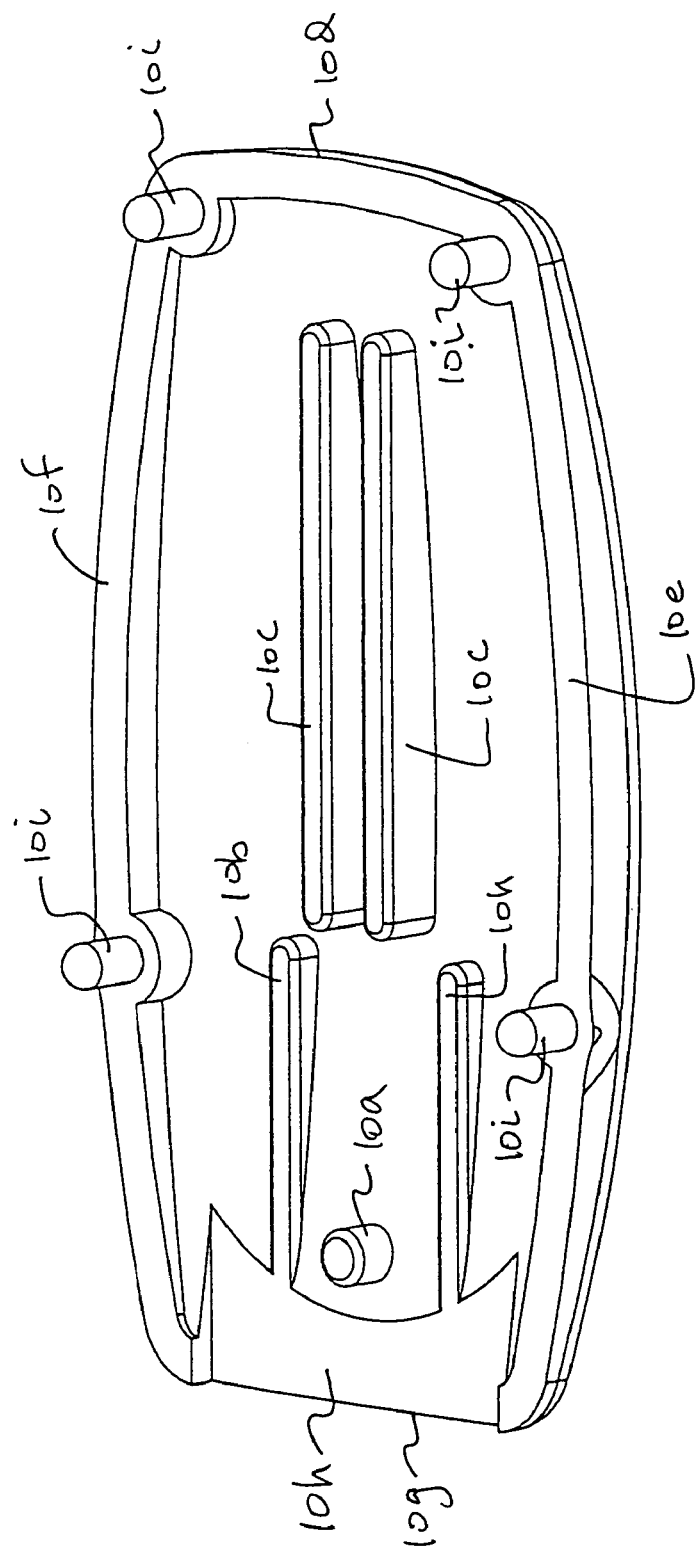
FIG. 20 shows a perspective view of the lancet body cover of FIG. 17.
Figure 23A:
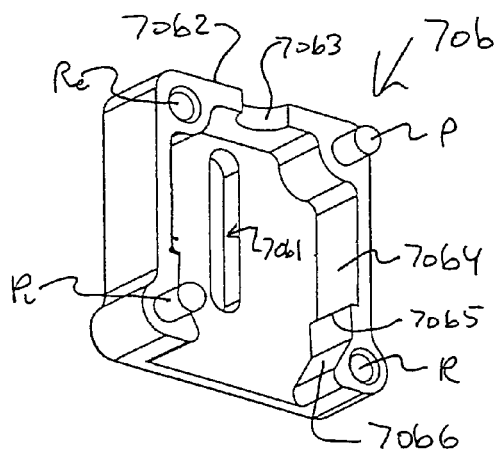
Figure 23B:
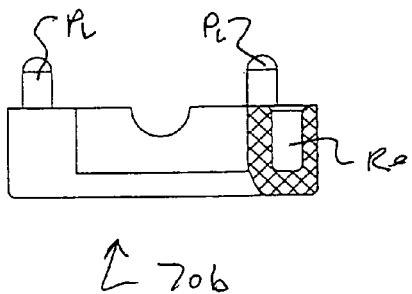
FIG. 23b shows an end view of FIG. 23a. A portion of the lower part is shown in cross-section.
Figure 23C:
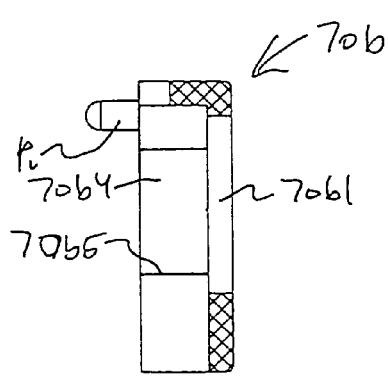
FIG. 23c shows a center cross-section view of the lower part shown in section E-E of FIG. 23d.
Figure 23D:
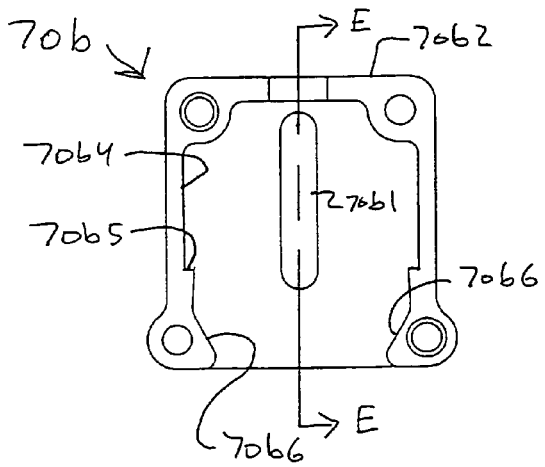
FIG. 23d shows another inside view of the lower portion of the skin engaging head.

Thus, movement of the skin engaging member 70 causes the automatic triggering of the device and causes the automatic retraction of both the lancet needle holding member 50 and the skin engaging member 70. All of the movements just described with respect to FIGS. 6-11 essentially occur in a fraction of a second. As discussed above, the movement of the holding member 50 is linearly guided by the flanges 10c and 20k whereas the movement of the skin engaging member 70 into the lancet body is linearly guided by the front opening, and specifically surfaces 10h, 201, and projections 10a, 20a, and recesses 70a1 and 70b1. As can be seen in FIG. 12, after use, the possibly contaminated skin engaging surface of plane P and the lancet needle LN are moved completely within the lancet body and cannot come into contact with the skin of the same user or of another user. This provides two levels of safety since both the lancet needle LN and the skin contact surface or plane P are covered and protected. Moreover, unlike most known prior art devices, the lancet device LD contains no mechanism for reloading and/or moving the holding member 50 and/or the skin engaging member 70 back into the position shown in e.g., FIG. 5, i.e., the lancet device LD cannot then be placed back into the trigger-set position because the device contains no mechanism for placing the holding member 50 back into the position shown in FIGS. 3 and 5. Indeed, the spring 40, by being coupled at both ends to the body and the holding member 50, and by ensuring that the holding member 50 assumes an intermediate position shown in FIG. 11 after use, ensures that the holding member 50 cannot be re-armed, and ensures that the holding member 50 (along with the lancet needle and the skin engaging member 70) are safely retained within the body.

Although not shown, the embodiment shown in FIGS. 1-12 can also be modified so that the device is triggered by a user activated trigger button instead of being automatically triggered by movement of the skin engaging member 70. In this regard, while continuing to utilize the movably skin engaging portion, such a device can utilize a trigger activation system, i.e., a trigger button, to manually trigger movement of the holding member. One non-limiting example of such a trigger activation system is disclosed in copending U.S. patent application Ser. No. 10/878,390 to SCHRAGA filed on Jun. 29, 2004, which published as US 2005/0288699, the disclosure of which is hereby expressly incorporated by reference in its entirety.

Figure 26A:
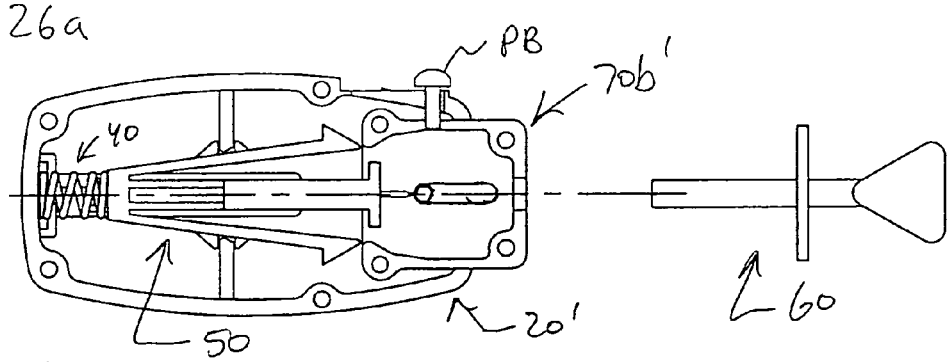
Figure 26B:
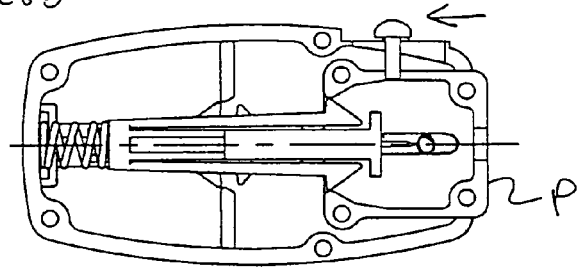
Figure 26C:
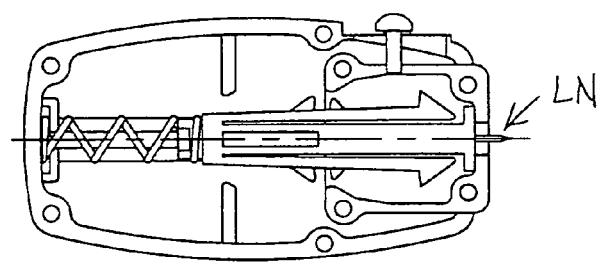
Figure 26D:
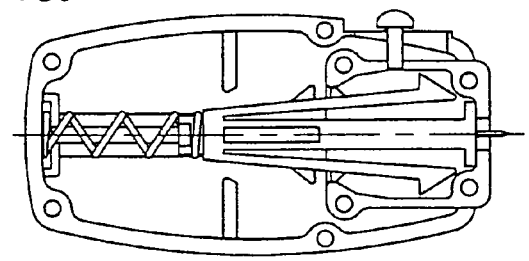
Figure 26E:
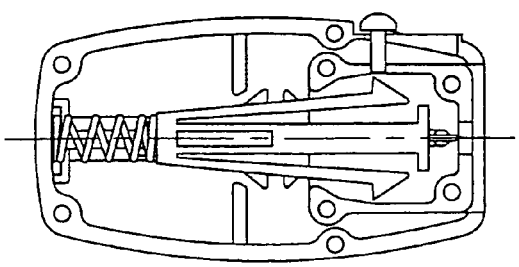
Figure 27B:
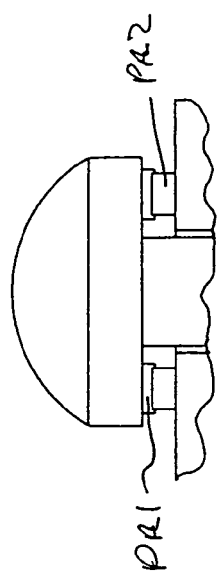
Figure 27A:
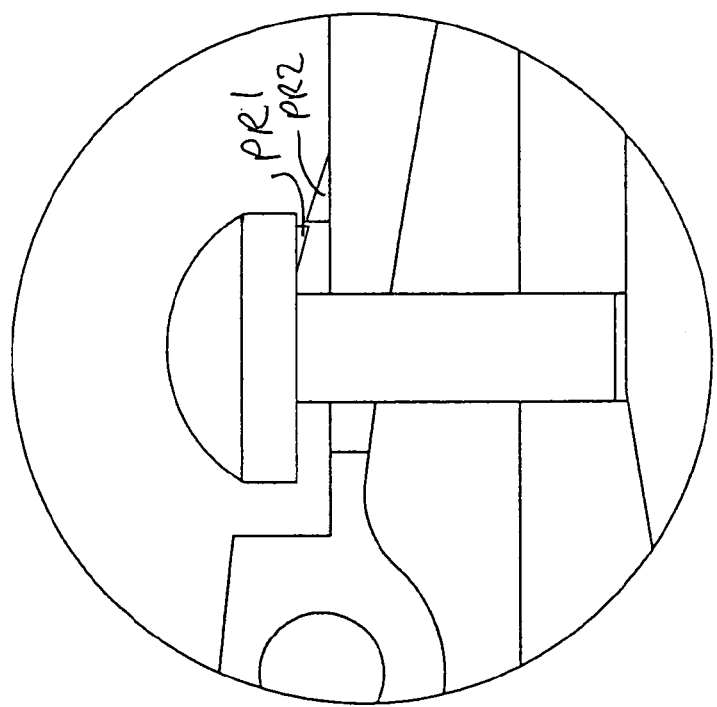
FIG. 27a shows an enlarged view of FIG. 26e and illustrates the mechanism for locking the button to the lancet body so that the skin engaging head cannot be moved forward again.

FIGS. 26a-27b show another non-limiting embodiment of the invention. This embodiment is similar to that of FIGS. 1-12 except that this embodiment allows a user to manually retract the skin engaging member (only lower portion 70b' is shown) via a push button PB. As can be seen in FIGS. 27a and 27b, the push button PB can be locked in the retracted position to ensure that the skin engaging member remains withdrawn into the device after use. In this regard, unlike the device shown in FIGS. 1-12, the skin engaging member of this embodiment does not utilize engagement between the portions 50e3, 50f3 and shoulders 70a5, 70b5 arranged within the skin engaging member. Instead, the arms 50e and 50f, and the holding member 50, are free to retract without causing automatic retraction of the skin engaging member.

The operation of this second non-limiting device will now be explained. FIGS. 26a-26e shows the lancet device LD with the lancet mechanism and skin engaging member in the loaded trigger set position. The holding member 50 and skin engaging member retains the loaded position of FIGS. 26a as a result of the tab portion 60 as was the case in the previous embodiment. FIG. 26a shows what happens when the tab portion 60 is removed, i.e., the lancet needle LN is now exposed and the lancet device LD can then be used and/or triggered. FIGS. 26b-26d show what happens when the skin engaging member is then retracted back under the action of the push-button PB, i.e., it is caused to slide into the lancet body. As with the previous embodiment, movement of the skin engaging member inwards causes inward deflection of the two arms 50e and 50f, owing to the sliding engagement between angled surfaces 50e4 and 50f4 and the rounded corners (i.e., the corners which correspond to corners 70a7 and 70b7). This inward deflection of the arms 50e and 50f causes the projections 50e1, 50e2 and 50f1, 50f2 to disengage from the retaining flanges of the lancet body (i.e., the flanges which correspond to flanges 20d and 20c), which in turn instantly allows the spring 40 to expand and cause the holding member 50 to move rapidly to the extended position (see FIG. 26c). The lancet needle LN is then free to penetrate the skin of a user in the position shown in FIG. 26c. The depth of penetration of the lancet needle LN is controlled by contact between surface 50a and inside surfaces of the skin engaging member (i.e., surfaces which correspond to surfaces 70a8 and 70b8). At this point, the arms 50e and 50f are again free to deflect outwardly owing to their inherent spring-like design, i.e., the memory of their original relaxed position shown in FIG. 26d. The projecting portions 50e3 and 50f3 can then engage inner surfaces of the skin engaging member. At essentially the same time, the spring 40 causes the holding member 50 to retract until it reaches the relaxed position shown in FIG. 26e. This retraction of the holding member 50 causes the projecting portions 50e3 and 50f3 to slidingly engage the inner surfaces of the skin engaging member during retraction. The user can then manually further retract the skin engaging member into the lancet device LD, until two locking projections PR1 of the push button PB engage two locking projections PR2 of the lancet body (see FIGS. 27a and 27b). In the position shown in FIG. 26e, the skin engaging member is locked in the retracted position and cannot be moved back to the position shown in FIG. 26a owing to the locking projections PR1, PR2.

Thus, manual movement of the skin engaging member causes the automatic triggering of the device and causes the automatic retraction of at least the lancet needle LN and/or the holding member 50. The skin engaging member can be fully retracted manually. Although not shown, the device can also utilize a second set of locking projections to as to prevent forward movement of the skin engaging member when and/or after it has reached the position shown in FIG. 26b. All of the movements just described with respect to FIGS. 26a-26e can essentially occur in a fraction of a second and/or in a very short period of time. Moreover, many of the movements of the inner workings of the lancet device LD also occur under the control of the user. As discussed above, the movement of the holding member 50 is linearly guided by the flanges (i.e., the flanges which correspond to flanges 10c and 20k) whereas the movement of the skin engaging member into the lancet body is linearly guided by the front opening and specifically surfaces and projections of the lancet body (i.e., surfaces which correspond to surfaces 10h, 20l and projections 10a, 20a and recesses 70a1 and 70b1). As can be seen in FIG. 26e, the possibly contaminated skin engaging surface of plane P and the lancet needle LN are completely arranged in the lancet body after use and cannot come into contact with the skin of the same user or of another user after use. This provides two levels of safety since both the needle LN and the skin contact surface P is covered and protected within the lancet device after use. Moreover, unlike known prior art devices, the lancet device LD contains no mechanism for reloading and/or moving the holding member 50 and/or the skin engaging member back into the position shown in e.g., FIG. 26a, i.e., the lancet device LD cannot then be placed back into the trigger set position because the device contains no mechanism for placing the holding member 50 back into the position shown in FIG. 26a. Indeed, the spring 40, by being coupled at both ends to the body and the holding member 50, and by ensuring that the holding member 50 assumes an intermediate position shown in FIG. 26e, ensures that the holding member 50 cannot be re-armed, and ensures that the holding member 50 (along with the lancet needle) are safely retained within the body.

FIGS. 28-30 show still another non-limiting embodiment of the invention. This embodiment is similar to that of FIGS. 1-12 except that this embodiment additionally utilizes the skin engaging member similar to that of the embodiment of FIGS. 26a-26e and an outer sleeve member OS which is biased towards an extended position via a rectangular-shaped spring SP1. At least one pivotally mounted (i.e., via pivot pin PP) door DR is mounted to the front inside portion of the sleeve OS. The sleeve OS is movably guided relative to the lancet body LB via four oppositely arranged projections GP and four oppositely arranged slots GS (see FIG. 29). Of course, the sleeve OS can be movably mounted to the lancet device in other ways without leaving the scope of the invention. Another spring SP2 biases the door DR towards an extended position (see FIG. 30). Moreover, although not shown, the invention contemplates using one or more other doors DR which can be, e.g., arranged on an opposite side of the outer sleeve OS.

The operation of this third non-limiting device will now be explained. FIG. 28 shows the lancet device LD with the lancet mechanism and skin engaging member (only lower part 70b" is shown) in the loaded trigger set position. The holding member 50 and skin engaging member retains the loaded position of FIG. 28 as a result of the tab portion 60, as was the case in the previous embodiments. FIG. 28 shows what happens when the tab portion 60 is removed, i.e., the lancet needle LN is now exposed and the lancet device can then be used and/or triggered. The lancet device LD is then ready to be used in the same way as was described with regard to FIGS. 1-12. That is, the skin engaging member is caused to be retracted back under the action of forcing the lancet device LD against the skin of the user. Movement of the skin engaging member inwards causes inward deflection of the two arms 50e and 50f owing to the sliding engagement between angled surfaces 50e4 and 50f4 and the rounded corners (i.e., the corners of the skin engaging member which correspond to corners 70a7 and 70b7). This inward deflection of the arms 50e and 50f causes the projections 50e1, 50e2 and 50f1, 50f2 to disengage from the retaining flanges (i.e., the flanges which correspond to flanges 20d and 20c), which in turn instantly allows the spring 40 to expand and cause the holding member 50 to move rapidly to the extended position. The lancet needle LN is then free to penetrate the skin of a user. The depth of penetration of the lancet needle LN is controlled by contact between surface 50a and inside surfaces of the skin engaging member (i.e., surfaces which correspond to surfaces 70a8 and 70b8). As this point, the arms 50e and 50f are again free to deflect outwardly owing to their inherent spring-like design, i.e., the memory of their original relaxed position shown in FIG. 28. The projecting portions 50e3 and 50f3 then engage inner surfaces of the skin engaging member. At essentially the same time, the spring 40 causes the holding member 50 to retract until it reaches a relaxed position. This retraction of the holding member 50 causes the projecting portions 50e3 and 50f3 to slidingly engage the inner surfaces of the skin engaging member.

During the retracting movement of the skin engaging member and the sleeve OS, the door DR will pivot forwardly once the shoulder SH of the skin engaging member retracts to a point just prior to disengaging the arms 50e and 50f from the retaining flanges of the lancet body. By the time that the device is triggered, the door DR has moved completely forwardly so that stop surface SS1 has contacted stop surface SS2, i.e., the door DR has assumed a generally vertical position. However, during continued retraction of the outer sleeve OS and the skin engaging member, the retraction of the outer sleeve OS stops at a point (due to contact between the projections GP and a rear stop surface of slots GS) while the retraction of the skin engaging member continues until triggering of the device is caused. Once triggered, the lancet device LD will then be removed by the user from the skin of the user. At this point, the outer sleeve OS is automatically forced back to the extended position shown in FIG. 28 under the action of the spring SP1. In this position, outer sleeve OS covers the skin engaging member and/or projects past it. Should the user then attempt reuse the device by forcing the outer sleeve OS against the user's skin, the stop surface SS4 will contact the stop surface SS2 and cause further movement of the skin engaging member into the lancet device LD. This configuration thus acts to prevent the skin engaging member from moving back outwards and/or prevents it from moving and/or projecting and/or extending forward of the front edge of the outer sleeve OS. In this position, therefore, the skin engaging member is essentially retained in the retracted position and cannot be moved back to the position shown in FIG. 28 owing to the outer sleeve OS and door DR. Moreover, as the lancet device LD contains no mechanism for moving the holding member 50 back to the armed position shown in FIG. 28, the device also cannot be triggered again.

Figure 32:
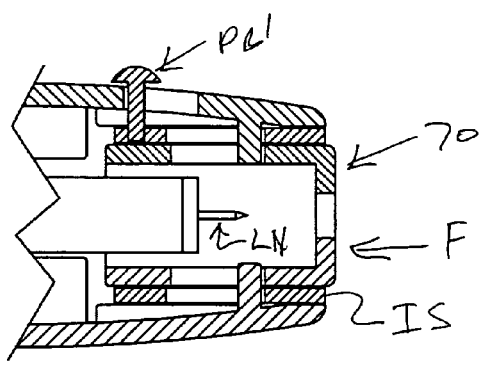
Figure 33:
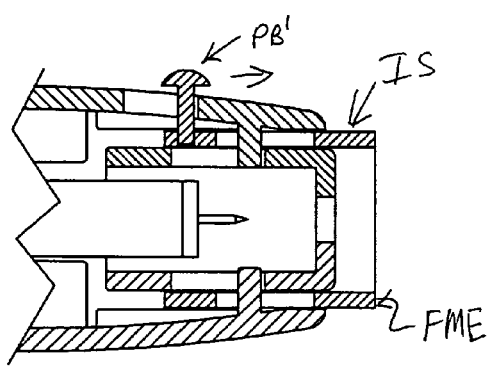
Figure 34:
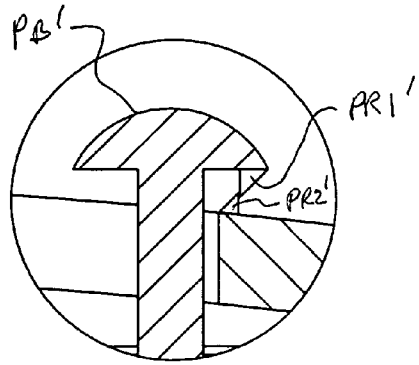

FIGS. 31-34 show another non-limiting embodiment of the invention. This embodiment is similar to that of FIGS. 1-12 except that this embodiment includes an inner sleeve IS and allows a user to manually extend the inner sleeve IS via a push button PB'. As can be seen in FIG. 34, the push button PB' can be locked in the extended forward position to ensure that the skin engaging member 70 is position back from a forward most edge FME of the lancet device after use. Although not shown, the invention contemplates using the inner sleeve IS on a lancet device LD which does not utilize the automatic skin engaging member retracting system used in the embodiment shown in FIGS. 1-12.

Figure 31:
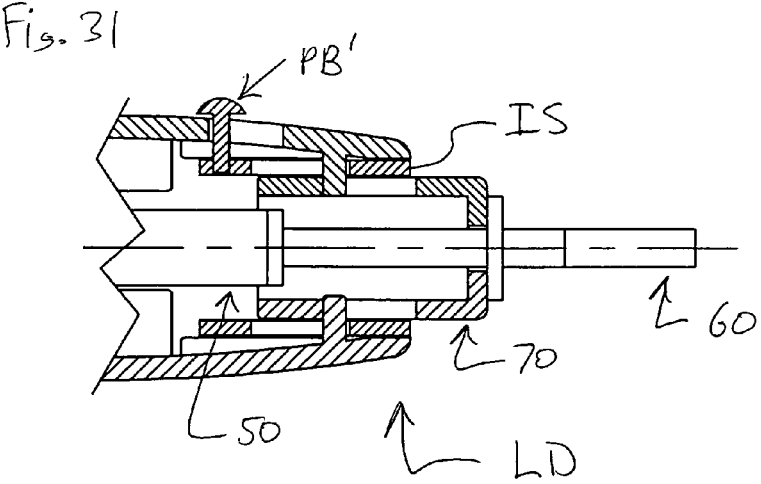

The operation of this fourth non-limiting device will now be explained. FIG. 31 shows the lancet device LD with the lancet mechanism and skin engaging member 70 in the loaded trigger-set position. The holding member 50 and skin engaging member 70 retains the loaded position of FIG. 31 as a result of the tab portion 60 as was the case of previous embodiments. FIG. 32 shows what happens when the tab portion 60 is removed, i.e., the lancet needle LN is now exposed and the lancet device LD can then be used and/or triggered. FIG. 32 also shows what happens when the skin engaging member 70 is then retracted back under the action of a force, i.e., it is caused to slide into the lancet body. As with the embodiment shown in FIGS. 1-12, movement of the skin engaging member 70 inwards causes inward deflection of the two arms 50e and 50f, owing to the sliding engagement between angled surfaces 50e4 and 50f4 and the rounded corners (i.e., the corners which correspond to corners 70a7 and 70b7). This inward deflection of the arms 50e and 50f causes the projections 50e1, 50e2 and 50f1, 50f2 to disengage from the retaining flanges of the lancet body (i.e., the flanges which correspond to flanges 20d and 20c), which in turn instantly allows the spring 40 to expand and cause the holding member 50 to move rapidly to the extended position. The lancet needle LN is then free to penetrate the skin of a user in the position. The depth of penetration of the lancet needle LN is controlled by contact between surface 50a and inside surfaces of the skin engaging member (i.e., surfaces which correspond to surfaces 70a8 and 70b8). As this point, the arms 50e and 50f are again free to deflect outwardly owing to their inherent spring-like design, i.e., the memory of their original relaxed position. The projecting portions 50e3 and 50f3 can then engage inner surfaces of the skin engaging member 70. At essentially the same time, the spring 40 causes the holding member 50 to retract until it reaches the relaxed position shown in FIG. 33. This retraction of the holding member 50 causes the projecting portions 50e3 and 50f3 to slidingly engage the inner surfaces of the skin engaging member during retraction. The user can then manually extend the inner sleeve IS from within the lancet device LD, until two locking projections PR1' (similar to that of FIGS. 27a-b and only one of which is shown) of the push button PB' engage two locking projections PR2' (only one of which is shown) of the lancet body. In the position shown in FIG. 33, the skin engaging member 70 is fully retracted and the inner sleeve IS is locked in the fully extended position and cannot be moved back to the position shown in FIGS. 31 and 32 owing to the locking projections PR1', PR2'.

Thus, movement of the skin engaging member causes the automatic triggering of the device and causes the automatic retraction of at least the lancet needle LN and/or the holding member 50. The inner sleeve IS can be fully extended manually. Although not shown, the device can also utilize a second set of locking projections to as to prevent forward movement of the skin engaging member 70 when and/or after it has reached the position shown in FIG. 32. All of the movements just described with respect to FIGS. 31-33 can essentially occur in a fraction of a second and/or in a very short period of time. Moreover, many of the movements of the inner workings of the lancet device LD also occur under the control of the user. As discussed above, the movement of the holding member 50 is linearly guided by the flanges (i.e., the flanges which correspond to flanges 10c and 20k) whereas the movement of the skin engaging member 70 and inner sleeve IS into and out of the lancet body is linearly guided by the front opening and specifically surfaces and projections of the lancet body (i.e., surfaces which correspond to surfaces 10h, 201 and projections 10a, 20a and recesses 70a1 and 70b1). As can be seen in FIG. 33, the possibly contaminated skin engaging surface of plane P and the lancet needle LN are completely arranged in the lancet body after use and cannot come into contact with the skin of the same user or of another user after use. This provides two levels of safety since both the needle LN and the skin contact surface P is covered and protected within the lancet device after use. Moreover, unlike known prior art devices, the lancet device LD contains no mechanism for reloading and/or moving the holding member 50 and/or the skin engaging member 70 and/or the inner sleeve IS back into the position shown in e.g., FIG. 31, i.e., the lancet device LD cannot then be placed back into the trigger set position because the device contains no mechanism for placing the holding member 50 back into the position shown in FIG. 31, and/or for placing the skin engaging member 70 back into the position shown in FIG. 31, and/or for placing the inner sleeve IS back into the position shown in FIGS. 31 and 32. Indeed, the spring 40, by being coupled at both ends to the body and the holding member 50, and by ensuring that the holding member 50 assumes an intermediate position, ensures that the holding member 50 cannot be re-armed, and ensures that the holding member 50 (along with the lancet needle) are safely retained within the body. Although not shown, the invention contemplates, instead of using a push button PB', utilizing a spring biased inner sleeve IS (biased in a manner similar to that shown in FIG. 28) which is caused to automatically move to the extended position when the skin engaging member 70 is moved to the position shown in FIG. 32.

All the parts of the lancet device, with the exception of the springs 40, SP1 and SP2 (which can be made of spring steel) and with the exception of the lancet needle (which can be a conventional metal needle), may be made from plastic materials and can be formed using conventional injection molding techniques or other known manufacturing methods. However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A single-use lancet device, comprising:
    a body;
    a skin engaging member being movable with respect to the body and comprising a lancet opening through which a lancet needle extends;
    a holding member movably mounted within the body and comprising a front end and a rear end;
    the holding member being movable at least between a retracted position and an extended position;
    a first stop surface that moves with the skin engaging member; and
    a second stop surface that moves with the holding member, wherein movement of the skin engaging member from an initial position to a triggering position causes the holding member to move towards the extended position,
    wherein, once caused to move to the extended position, the holding member is prevented from moving back to the retracted position, and
    wherein after a triggering of the lancet device, the skin engaging member is caused to automatically move towards a retracted position and thereby prevent reuse of the single-use lancet device.

2. The lancet device of claim 1, further comprising a spring, wherein the spring causes the holding member to move to the extended position and prevents the holding member from moving back to the retracted position.

3. The lancet device of claim 2, wherein the spring causes the skin engaging member to move to a retracted position, whereby the skin engaging member is disposed within the body.

4. The lancet device of claim 1, further comprising a spring which causes the skin engaging member and the holding member to move into the body after the lancet device is triggered.

5. The lancet device of claim 1, further comprising a spring which causes movement of the holding member between the retracted position and the extended position and between the extended position and an intermediate position.

6. The lancet device of claim 1, further comprising a spring which causes the holding member to move away from the lancet opening after the lancet device is triggered.

7. The lancet device of claim 6, wherein the holding member causes the skin engaging member to move into the body after the lancet device is triggered.

8. The lancet device of claim 1, wherein the holding member causes the skin engaging member to move into the body after the lancet device is triggered.

9. The lancet device of claim 1, further comprising a compression spring for biasing the holding member towards the extended position.

10. The lancet device of claim 9, wherein the compression spring comprises one end that is fixed to the rear end of the holding member and another end that is fixed to the body.

11. The lancet device of claim 9, wherein the compression spring comprises one end that is connected to the holding member and another end that is connected to the body.

12. The lancet device of claim 1, wherein the lancet device is automatically triggered by movement of the skin engaging portion.

13. The lancet device of claim 1, wherein the body comprises an upper housing part and a lower housing part.

14. The lancet device of claim 13, wherein the upper housing part comprises a cover and the lower housing part comprises a main body portion.

15. The lancet device of claim 1, wherein the holding member comprises the lancet needle and at least one deflectable arm.

16. The lancet device of claim 1, wherein the holding member comprises at least one integrally formed deflectable arm.

17. The lancet device of claim 1, wherein the holding member comprises two oppositely arranged integrally formed deflectable arms.

18. The lancet device of claim 1, wherein the holding member comprises a mechanism for releasably engaging with at least one flange fixed inside the body.

19. The lancet device of claim 1, wherein the holding member comprises two mechanisms for releasably engaging with two flanges fixed inside the body.

20. The lancet device of claim 19, wherein the holding member comprises two oppositely arranged integrally formed deflectable arms.

21. The lancet device of claim 20, wherein one of the two mechanisms is arranged on one of the two integrally formed deflectable arms and another of the two mechanisms is arranged on another of the two integrally formed deflectable arms.

22. The lancet device of claim 1, wherein the holding member comprises two mechanisms for releasably engaging with two projections fixed inside the body.

23. The lancet device of claim 22, wherein the holding member comprises two oppositely arranged deflectable arms.

24. The lancet device of claim 23, wherein one of the two mechanisms is arranged on one of the two deflectable arms and another of the two mechanisms is arranged on another of the two deflectable arms.

25. The lancet device of claim 1, wherein the holding member comprises two oppositely arranged deflectable arms, each deflectable arm comprising two projections and a space disposed between the two projections, whereby each space receives therein a projecting portion fixed within the body when the holding member is in the retracted position.

26. The lancet device of claim 1, wherein the holding member comprises a removable tab portion.

27. The lancet device of claim 1, wherein the holding member comprises a mechanism for preventing accidental triggering of the lancet device.

28. The lancet device of claim 27, wherein the mechanism for preventing accidental triggering of the lancet device comprises a removable tab portion coupled to the front end of the holding member.

29. The lancet device of claim 1, wherein the front end of the holding member holds the lancet needle.

30. The lancet device of claim 1, wherein the lancet needle projects from the front end of the holding member.

31. The lancet device of claim 1, wherein the second stop surface is arranged on the front end of the holding member and behind a tip of the lancet needle.

32. The lancet device of claim 1, further comprising a removable trigger preventing device, whereby the lancet device cannot be triggered without removing the trigger preventing device.

33. The lancet device of claim 1, further comprising a removable trigger preventing device, whereby the lancet device cannot be triggered or used without disconnecting the trigger preventing device from the front end of the holding member.

34. The lancet device of claim 33, wherein the removable trigger preventing device comprises a gripping portion, a flange which engages the skin engaging member, and an end adapted to cover the lancet needle.

35. The lancet device of claim 34, wherein the removable trigger preventing device comprises a gripping portion, a flange which engages the skin engaging member, and an end removably connected to the front of the holding member and adapted to cover the lancet needle.

36. The lancet device of claim 1, wherein the skin engaging member is configured to slide into the body during triggering of the lancet device.

37. The lancet device of claim 1, wherein the skin engaging member comprises at least one straight and/or planar surface which slidably engages at least one straight and/or planar surface of the body during triggering of the lancet device.

38. The lancet device of claim 1, wherein the skin engaging member comprises a generally rectangular cross-sectional shape.

39. The lancet device of claim 1, wherein an inside surface of the skin engaging member comprises the first stop surface.

40. The lancet device of claim 1, wherein the body comprises a mechanism for guiding an axial movement of the holding member.

41. The lancet device of claim 40, wherein the mechanism for guiding comprises at least two projecting flanges arranged inside the body.

42. The lancet device of claim 41, wherein the holding member comprises at least one projecting portion which moves with a space disposed between the at least two projecting flanges.

43. The lancet device of claim 40, wherein the mechanism for guiding comprises oppositely arranged projecting flanges arranged inside the body.

44. The lancet device of claim 43, wherein the holding member comprises two oppositely arranged projecting portions which move with spaces disposed between the oppositely arranged projecting flanges.

45. The lancet device of claim 40, wherein the holding member comprises ends which engage internal shoulders of the skin engaging member when the holding member moves from the extended position to an intermediate position.

46. The lancet device of claim 1, wherein the body comprises a two-piece body.

47. The lancet device of claim 1, wherein the skin engaging member comprises at least one recess which receives therein a projection extending into the body.

48. The lancet device of claim 1, wherein the skin engaging member comprises oppositely arranged recesses which each receive therein a projection fixed to the body.

49. A method of puncturing a surface of skin using the lancet device of claim 1, the method comprising:
disposing the skin engaging member of the lancet device against a user's skin;
moving the skin engaging portion relative to the body so as to cause automatic triggering of the lancet device, whereby the lancet needle is caused to penetrate the user's skin; and
preventing the user from moving the holding member to the retracted position.

50. A method of puncturing a surface of skin using the lancet device of claim 1, the method comprising:
disposing the skin engaging member of the lancet device against a user's skin;
moving the skin engaging portion relative to the body so as to cause automatic triggering of the lancet device, whereby the lancet needle is caused to penetrate the user's skin;
preventing the user from moving the holding member to the retracted position; and
preventing the user from moving the skin engaging member to the initial position.

51. A method of puncturing a surface of skin using the lancet device of claim 1, the method comprising:
disposing the skin engaging member of the lancet device against a user's skin;
moving the skin engaging portion relative to the body so as to cause automatic triggering of the lancet device, whereby the holding member is caused to move to the extended position and the lancet needle is caused to penetrate the user's skin,
wherein, after triggering, the user is at least one of prevented from moving the holding member to the retracted position and prevented from moving the skin engaging member to the initial position.

52. A method of using the lancet device of claim 1, the method comprising:
removing a triggering prevention device;
disposing the skin engaging member of the lancet device against a user's skin; and
moving the skin engaging member relative the body, wherein the moving automatically causes movement of the holding member towards the extended position.

53. A method of using the lancet device of claim 1, the method comprising:
- removing a triggering prevention device;
- disposing the skin engaging member of the lancet device against a user's skin; and
- non-rotatably moving the skin engaging member relative to the body,
- wherein the non-rotatably moving automatically causes movement of the holding member towards the extended position.

54. A single-use lancet device, comprising:
- a body;
- a skin engaging member being at least partially disposed inside the body and comprising a lancet opening through which a lancet needle extends;
- a holding member movably mounted within the body and comprising a front end and a rear end;
- the holding member being movable at least between a retracted position and an extended position;
- a first stop surface that moves with the skin engaging member; and
- a second stop surface that moves with the holding member,
- wherein movement of the skin engaging member from an initial position to a triggering position automatically causes the holding member to move towards the extended position, and
- wherein after a triggering of the lancet device, the skin engaging member is caused to automatically move towards a retracted position and thereby prevent reuse of the single-use lancet device.

55. The lancet device of claim 54, wherein, once caused to move to the extended position, the holding member is prevented from moving back to the retracted position.

56. The lancet device of claim 54, further comprising a spring, wherein the spring causes the holding member to move to the extended position and prevents the holding member from moving back to the retracted position.

57. The lancet device of claim 54, further comprising a spring which causes movement of the holding member between the retracted position and the extended position and between the extended position and an intermediate position.

58. The lancet device of claim 54, wherein the holding member causes the skin engaging member to move further into the body after the lancet device is triggered.

59. The lancet device of claim 54, wherein the holding member causes the skin engaging member to move into the body after the lancet device is triggered.

60. A single-use lancet device, comprising:
- a body;
- a non-rotatably and slidably mounted skin engaging member being at least partially disposed inside the body;
- the skin engaging member comprising a lancet opening through which a lancet needle extends;
- a holding member movably mounted within the body and comprising a front end and a rear end; and
- the holding member being movable at least between a retracted position and an extended position,
- wherein movement of the skin engaging member further into the body automatically causes the holding member to move towards the extended position, and
- wherein after a triggering of the lancet device, the skin engaging member is caused to automatically move towards a retracted position and thereby prevent reuse of the single-use lancet device.

61. A single use or disposable lancet device, comprising:
- a body;
- a movable skin engaging member being at least partially disposed inside the body and comprising a lancet opening through which a lancet needle extends; and
- a holding member which can move at least between a retracted position and an extended position,
- wherein the skin engaging member is structured and arranged to retract into the body, and
- wherein after a triggering of the lancet device, the skin engaging member is caused to automatically move by the holding member towards a retracted position and thereby prevent reuse of the single-use or disposable lancet device.

62. A lancet device, comprising:
- a body;
- a skin engaging member structured and arranged to cause triggering of the lancet device and prevent reuse of the lancet device;
- a lancet opening through which a lancet needle extends;
- a holding member which can move at least between a retracted position and an extended position;
- the holding member being structured and arranged to cause the skin engaging member to move further into the body from a triggering position after the lancet device is triggered; and
- at least one of:
  - at least after the holding member moves to the extended position, the skin engaging member is covered by at least one of an outer sleeve and a portion of the body;
  - at least after triggering of the lancet device, a front edge of at least one of an outer sleeve and a portion of the body extends forwardly of a skin contact surface of the skin engaging member;
  - at least after the holding member moves to the extended position, the skin engaging member is covered by at least one of an inner sleeve and a portion of the body; and
  - at least after triggering of the lancet device, a front edge of at least one of an inner sleeve and a portion of the body extends forwardly of a skin contact surface of the skin engaging member.

63. A single-use lancet device, comprising:
- a body;
- a holding member movably mounted within the body;
- a skin engaging member comprising a lancet opening, having, in an initial position, one portion arranged in the body and another portion arranged outside the body, and being configured to prevent reuse of the single-use lancet device,
- wherein the single-use lancet device is triggered by movement of the skin engaging member to a triggering position from the initial position, and
- wherein the holding member is structured and arranged to cause the skin engaging member to move further into the body from the triggering position after the lancet device is triggered.

64. A single-use lancet device, comprising:
- a body;
- a skin engaging member being movable with respect to the body and comprising a lancet opening through which a lancet needle extends;
- a holding member movably mounted within the body and comprising a front end and a rear end;
- the holding member being movable at least between a retracted position and an extended position;

a first stop surface that moves with the skin engaging member; and
a second stop surface that moves with the holding member,
wherein movement of the skin engaging member from an initial position to a triggering position causes the holding member to move towards the extended position,
wherein, once caused to move to the extended position, the holding member is prevented from moving back to the retracted position,
wherein after a triggering of the lancet device, the skin engaging member is caused to automatically move towards a retracted position, and
wherein, once caused to move to the triggering position, the skin engaging member is prevented from moving back to the initial position.

65. A single-use lancet device, comprising:
a body;
a skin engaging member being at least partially disposed inside the body and comprising a lancet opening through which a lancet needle extends;
a holding member movably mounted within the body and comprising a front end and a rear end;
the holding member being movable at least between a retracted position and an extended position;
a first stop surface that moves with the skin engaging member; and
a second stop surface that moves with the holding member,
wherein movement of the skin engaging member from an initial position to a triggering position automatically causes the holding member to move towards the extended position,
wherein after a triggering of the lancet device, the skin engaging member is caused to automatically move towards a retracted position, and
wherein, once caused to move to the triggering position, the skin engaging member is prevented from moving back to the initial position.

* * * * *